(12) United States Patent
Tajima et al.

(10) Patent No.: US 6,664,281 B1
(45) Date of Patent: Dec. 16, 2003

(54) CARBOXYLIC ACID DERIVATIVES AND DRUGS CONTAINING THE SAME AS THE ACTIVE INGREDIENT

(75) Inventors: Hisao Tajima, Osaka (JP); Yoshisuke Nakayama, Osaka (JP); Daikichi Fukushima, Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/763,575

(22) PCT Filed: Aug. 25, 1999

(86) PCT No.: PCT/JP99/04580

§ 371 (c)(1), (2), (4) Date: Feb. 26, 2001

(87) PCT Pub. No.: WO00/12491

PCT Pub. Date: Mar. 9, 2000

(30) Foreign Application Priority Data

Aug. 27, 1998 (JP) .......................................... P 10-241208
Oct. 22, 1998 (JP) .......................................... P 10-300233

(51) Int. Cl.[7] ........................ C07D 263/32; A61K 31/42
(52) U.S. Cl. ........................ 514/374; 548/183; 548/235; 548/236
(58) Field of Search ................................ 548/235, 236, 548/183; 514/374

(56) References Cited

FOREIGN PATENT DOCUMENTS

| EP | 410244 | 1/1991 |
| JP | 62-260827 | 11/1987 |
| JP | 5-163245 | * 6/1993 |
| JP | 8-325182 | 12/1996 |
| JP | 11-43461 | * 2/1999 |

OTHER PUBLICATIONS

International Search Report.

* cited by examiner

*Primary Examiner*—Robert Gerstl
(74) *Attorney, Agent, or Firm*—Sughrue Mion, PLLC

(57) ABSTRACT

A peroxisome proliferator activated receptor regulator containing a carboxylic acid derivative of formula (I)

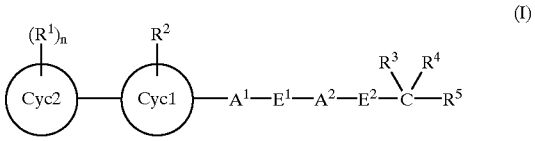

(wherein all symbols are as defined in the specification), a non-toxic acid thereof or a hydrate thereof as active ingredient.

Because of having an effect of regulating PPAR, a compound of formula (I) is useful as a hypoglycemic agent, a hypolipidemic agent, a preventive and/or a remedy for diseases associating metabolic disorders (diabetes, obesity, syndrome X, hypercholesterolemia, hyperlipoproteinemia, etc.), hyperlipemia, atherosclerosis, hypertension, circulatory diseases, overeating, coronary heart diseases, etc., an HDL cholesterol-elevating agent, an LDL cholesterol and/or VLDL cholesterol-lowering agent and a drug for relief from risk factors of diabetes or syndrome X.

13 Claims, No Drawings

CARBOXYLIC ACID DERIVATIVES AND DRUGS CONTAINING THE SAME AS THE ACTIVE INGREDIENT

TECHNICAL FIELD

The present invention relates to a carboxylic acid derivative and a peroxisome proliferator activated receptor regulator containing carboxylic acid derivative as active ingredient.

More particularly, the present invention relates to a compound of the formula

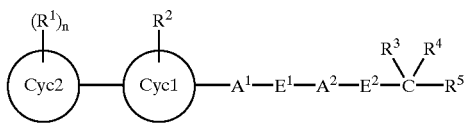

(I)

(wherein, all the symbols are the same meanings as defined hereafter), non-toxic salt thereof and hydrate thereof, process for producing the same and peroxisome proliferator activated regulator containing the same as an active ingredient.

BACKGROUND

Recently in the study of transcription factors concerned with marker genes expression in adipocytes differentiation, peroxisome proliferator activated receptor (abbreviated as PPAR hereinafter), which is one of intranucler receptors, has been focused. cDNAs of PPAR were cloned from various kinds of animals, and plural isoform genes were found, particularly in mammals three types of isoforms ($\alpha$, $\delta$, $\gamma$) are known (see J. Steroid Biochem. Molec. Biol., 51, 157 (1994); Gene Expression,. 4, 281 (1995); Biochem Biophys. Res. Commun., 224, 431 (1996); Mol. Endocrinology., 6, 1634 (1992)). PPAR$\gamma$ isoform is predominantly expressed in adipose tissues, immune cells, adrenal gland, spleen, small intestine. PPAR$\alpha$ isoform is mainly expressed in adipose tissue, liver, retina, and PPAR$\delta$ isoform is widely expressed without specificity for tissue (see Endocrinology., 137, 354 (1996)).

On the other hand, the following thiazolidine derivatives are known as agents for the treatment of non-insulin dependent diabetes mellitus (NIDDM) and are hypoglycemic agents which are used for the improvement of hyperglycemia in the patients suffering from diabetes. They are also effective for the improvement of hyperinsulinemia, glucose tolerance and decrease of serum lipid and therefore they are thought to be considerably hopeful as agents for the treatment of insulin resistance.

pioglitazone

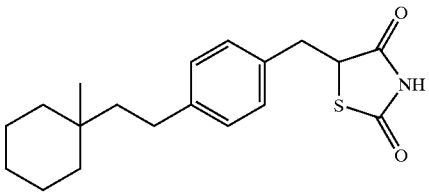

ciglitazone

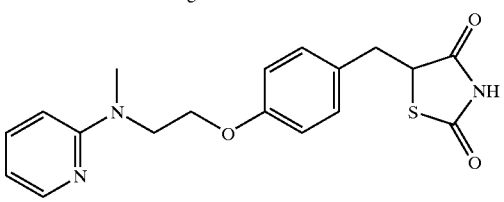

BRL49653

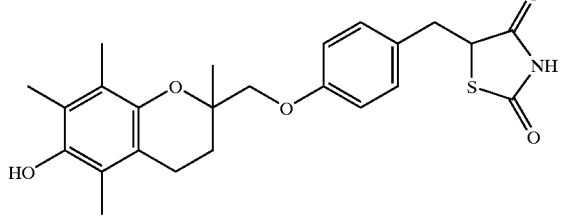

troglitazone

One of the target proteins in the cells of these thiazolidine derivatives is exactly PPAR$\gamma$ and it is resolved that they enhance the transcription activity of PPAR$\gamma$ (see Endocrinology., 137, 4189 (1996); Cell., 83, 803 (1995); Cell., 83, 813 (1995); J. Biol. Chem., 270, 12953 (1995)). Therefore, a PPAR$\gamma$ activator (agonist) which enhances its transcription activity is thought to be hopeful as a hypoglycemic agent and/or a hypolipidemic agent. Furthermore, since a PPAR$\gamma$ agonist is known to promote the expression of PPAR$\gamma$ protein itself (Genes & Development., 10, 974 (1996)), an agent which increases the expression of PPAR$\gamma$ protein itself as well as PPAR$\gamma$ activating agent is also thought to be clinically useful.

Among all of nuclear receptors, PPAR$\gamma$ is related to adipocytes differentiation (see J. Biol. Chem., 212, 5637 (1997) and Cell., 83, 803 (1995)). It is known that thiazolidine derivatives which activate this receptor promote adipocytes differentiation. Recently it was reported that thiazolidine derivatives increase fat mass and cause man to gain weight and to become obese (see Lancet., 349, 952 (1997)). Therefore, it is also thought that antagonists which inhibit PPAR$\gamma$ activity and agents that decrease the expression of PPAR$\gamma$ protein itself are also clinically applicable. On the other hand, a compound that phosphorylates PPAR$\gamma$ protein and decreases its activity is reported (Science., 274, 2100 (1996)). This implies that an agent which does not bind on PPAR$\gamma$ protein as a ligand, but inhibits its activity is also clinically applicable.

From these, PPAR$\gamma$ activators (agonists) and PPAR$\gamma$ regulators for its expression that can increase the expression of the protein itself are expected to be useful as hypoglycemic agents, hypolipidemic agents, and agents for prevention and/or treatment of diseases associated with metabolic disorders such as diabetes, obesity, syndrome X, hypercholesterolemia and hyperlipoproteinemia etc., hyperlipidemia, atherosclerosis, hypertension, circulatory diseases and overeating etc.

On the other hand, antagonists that inhibit the transcription activity of PPARγ or PPARγ regulators that inhibit the expression of the protein itself are expected to be useful as hypoglycemic agents and agents for prevention and/or treatment of diseases associated with metabolic disorders such as diabetes, obesity and syndrome X etc., hyperlipidemia, atherosclerosis, hypertension and overeating etc.

The following fibrate compound (e.g. chlofibrate) is known as a hypolipidemic agent.

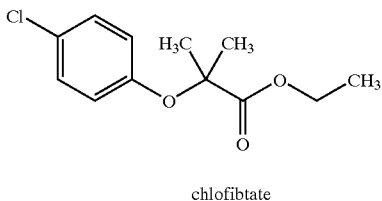

chlofibtate

And, it is also resolved that one of the target proteins in the cells of fibrate compounds is PPARα (See Nature., 347, 645 (1990); J. Steroid Biochem. Molec. Biol., 51, 157 (1994); Biochemistry., 32, 5598 (1993)). From these facts, PPARα regulators which can be activated by fibrate compounds are thought to have a hypolipidemic effect, and so they are expected to be useful as agents for prevention and/or treatment of hyperlipidemia etc.

Besides, it has been recently reported that PPARα possesses anti-obese activity in the specification of WO 9736579. In addition, it was reported that the elevation of high density lipoprotein (HDL) cholesterol level and the reduction of low density lipoprotein (LDL) cholesterol, very low density lipoprotein (VLDL) cholesterol and triglyceride levels were induced by activation of PPARα (J. Lipid Res., 39, 17 (1998)). It was also reported that composition of fatty acids in blood, hypertension and insulin resistance were improved by administration of bezafibrate which is one of bezafibrate compounds (Diabetes., 46, 348 (1997)).

Therefore, agonists that activate PPARα and PPARα regulators that promote expression of PPARα protein itself are useful as hypolipidemic agents and agents for treatment of hyperlipidemia, and are expected to have HDL cholesterol level-elevating effect, LDL cholesterol and/or VLDL cholesterol levels-lowering effect, inhibition on the progress of atherosclerosis and anti-obese effect. Therefore, they are thought to be hopeful agents for the treatment and/or prevention of diabetes as hypoglycemic agents, for the improvement of hypertension, for the relief from risk factor of syndrome X and for the prevention of occurrence of ischemic coronary diseases.

On the other hand, few reports are found on ligands that activate PPARδ significantly or on biological activities associated with PPARδ

PPARδ is sometimes called PPARβ, or it is also called NUC1 in human. Until now, as for activity of PPARδ, it is disclosed in the specification of WO 9601430 that hNUC1B (PPAR subtype whose structure is different from that of human NUC1 in one amino acid) inhibited the transcription activities of human PPARα and thyroid hormone receptor. Recently in the specification of WO 9728149, it was reported that the compounds, which possessed high affinity to PPARδ protein and which could activate PPARδ significantly (i.e. agonists) were found out and that they had HDL (high density lipoprotein) cholesterol level-elevating activity. Therefore, agonists that can activate PPARδ are expected to have HDL cholesterol level-elevating effect, and so they are expected to be useful for the inhibition on the progress of atherosclerosis and treatment thereof, as hypolipidemic agents and hypoglycemic agents, for the treatment of hyperlipidemia, as hypoglycemic agents, for the treatment of diabetes, for the relief from risk factor of syndrome X, and for the prevention of occurrence of ischemic coronary diseases.

As for PPAR regulators, the following compounds were reported besides the above-mention thiazolidine derivatives and fibrate compounds.

For example, in WO9731907, it is disclosed that the compounds of the formula (A)

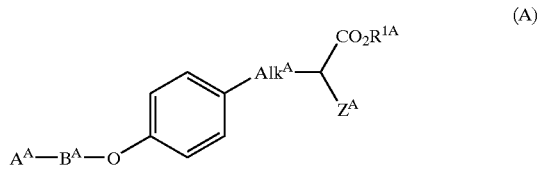

(wherein, $A^A$ is phenyl, in which the said phenyl may be substituted with one or more substituent(s) selected from group consisting of halogen, C1–6 alkyl, C1–3 alkoxy, C1–3 fluoroalkoxy, nitrile or —$NR^{7A}R^{8A}$ ($R^{7A}$ and $R^{8A}$ each independently, is hydrogen or C1–3 alkyl);

$B^A$ is (5- or 6-membered heterocyclic ring containing at least one hetero atom selected from O, N and S)-C1–6 alkylene-, in which the said heterocyclic ring may be substituted with C1–3 alkyl;

$Alk^A$ is C1–3 alkylene;

$R^{1A}$ is hydrogen or C1–3 alkyl;

$Z^A$ is —(C1–3 alkylene)phenyl or —$NR^{3A}R^{4A}$)

or pharmaceutically acceptable salts thereof possess PPARγ agonist activity (the necessary parts in explanation of symbols are shown).

On the other hand, in JP-A-9-323982, it is disclosed that the propionic acid derivatives of the formula (B)

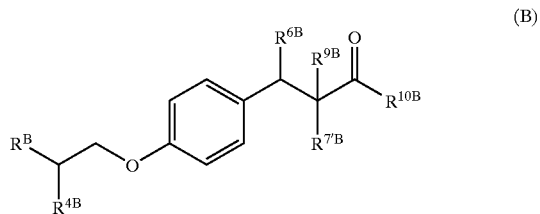

(wherein, $R^8$ is

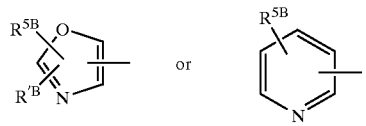

(wherein, $R^8$ is substituted or unsubstituted aromatic hydrocarbon, substituted or unsubstituted aliphatic hydrocarbon ring, substituted or unsubstituted heterocyclic ring or substituted or unsubstituted condensed heterocyclic ring, $R^{5B}$ is lower alkyl), $R^{4B}$ is hydrogen or lower alkyl, $R^{6B}$ is hydrogen or $R^{6B}$ and $R^{9B}$ taken together form double bond, $R^{7B}$ is hydrogen, hydroxy, carboxy, acyl, substituted or unsubstituted alkoxycarbonyl, substituted or unsubstituted lower alkyl, substituted or unsubstituted carbamoyl, substituted or unsubstituted aryloxycarbonyl, substituted or unsubstituted aralkyloxycarbonyl or —$Y^B$—$R^{8B}$ (in which $Y^B$ is —NH— or O, $R^{8B}$ is substituted or unsubstituted acyl, substituted or unsubstituted alkoxycarbonyl, aryloxycarbonyl or aralkyloxycarbonyl), $R^{9B}$ is hydrogen, substituted or unsubstituted lower alkyl or substituted or unsubstituted lower alkoxycarbonyl, $R^{10B}$ is hydroxy, substituted or unsubstituted amino, substituted or unsubstituted lower alkoxy, substituted or unsubstituted lower alkyl, substituted or unsubstituted aryloxy or substituted or unsubstituted aralkyloxy) or pharmaceutically acceptable salts thereof possess hypoglycemic action and hypolipidemic action. In addition, JP-A-8-325264, JP-A-8-325250, WO9638415 and WO9800137 have also disclosed that analogous compounds possess hypoglycemic action and hypolipidemic action.

DISCLOSURE OF THE INVENTION

As the result of energetic investigation in order to find compounds possessing regulating action on PPAR, the present inventors have found that the purpose has been accomplished by the compound of the formula (I) and have completed the present invention.

The present invention relates to, (1) a compound of the formula (I)

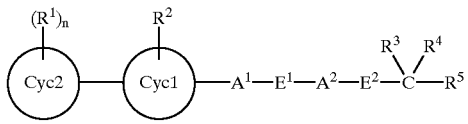

(I)

(wherein, $A^1$ is C1–4 alkylene, $A^2$ is C2–8 alkylene, C3–8 alkenylene or C3–8 alkynylene (with the proviso that (a) when $E^2$ is —O— or —S(O)$_m$—, $A^2$ represent neither C3 alkenylene nor C3 alkynylene and (b) each carbon atom in $A^2$ which is connected to $E^1$ and $E^2$ in which $E^2$ is O— or —S(O)$_m$— does not possess double bond), $E^1$ is —O— or —S—, $E^2$ is —CH$_2$—, —O— or —S(O)$_m$—, m is 0, 1 or 2, each $R^1$ in $(R^1)$n independently, is hydrogen, C1–8 alkyl, halogen, C1–4 alkoxy, C1–4 alkylthio, nitro, $NR^7R^8$ (in which $R^7$ and $R^8$ each independently, is C1–4 alkyl), cyano, trifluoromethyl, trifluoromethyloxy, carbocyclic ring or heterocyclic ring (in which carbocyclic ring and heterocyclic ring may be substituted with the group selected from C1–4 alkyl, C1–4 alkoxy, halogen or trifluoromethyl), $R^2$ is hydrogen, C1–8 alkyl, halogen, C1–4 alkoxy, C1–4 alkylthio, nitro, $NR^7R^8$ (in which $R^7$ and $R^8$ each independently, is C1–4 alkyl), cyano, trifluoromethyl or trifluoromethyloxy, $R^3$ and $R^4$ each independently, is hydrogen or C1–4 alkyl or $R^3$ and $R^4$ taken together with carbon atom to which is attached represents C3–7 cycloalkylene, $R^5$ is —COOR$^9$ (in which $R^9$ is hydrogen or C1–4 alkyl) or heterocyclic ring which is equivalent to carboxylic acid,

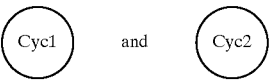

each independently, is carbocyclic ring or heterocyclic ring and n is 1–3)

or non-toxic salt thereof, or hydrate thereof, (2) a peroxisome proliferator activated receptor regulator comprising, as an active ingredient, a compound of the formula (I) or non-toxic salt thereof, or hydrate thereof, and (3) a process for producing a compound of the formula (I).

DETAILED EXPLANATION

Unless otherwise specified, all isomers are included in the present invention. For example, alkyl, alkoxy, alkylthio, alkylene, alkenylene and alkynylene group includes straight or branched ones. In addition, isomers on double bond, ring, fused ring (E-, Z-, cis-, trans-isomer), isomers generated from asymmetric carbon atom(s) (R-, S-, α-, β-isomer, enantiomer, diastereomer), optically active isomers (D-, L-, d-, l-isomer), polar compounds generated by chromatographic separation (more polar compound, less polar compound), equilibrium compounds, mixtures thereof at voluntary ratios and racemic mixtures are also included in the present invention.

In the formula (I), C1–4 alkylene represented by $A^1$ means methylene, ethylene, trimethylene, tetramethylene and isomers thereof.

In the formula (I), C1–4 alkyl represented by $R^3$, $R^4$, $R^7$, $R^8$ and $R^9$ or C1–4 alkyl as a substituent of carbocyclic ring or heterocyclic ring represented by $R^1$ means methyl, ethyl, propyl, butyl and isomers thereof.

In the formula (I), C1–8 alkyl represented by $R^1$ and $R^2$ means methyl, ethyl, propyl, butyl, pentyl, hexyl, heptyl, octyl and isomers thereof.

In the formula (I), C1–4 alkoxy represented by $R^1$ and $R^2$ or C1–4 alkoxy as a substituent of carbocyclic ring or heterocyclic ring represented by $R^1$ means methoxy, ethoxy, propoxy, butoxy and isomers thereof.

In the formula (I), C1–4 alkylthio represented by $R^1$ and $R^2$ means methylthio, ethylthio, propylthio, butylthio and isomers thereof.

In the formula (I), C2–8 alkylene represented by $A^2$ means ethylene, trimethylene, tetramethylene, pentamethylene, hexamethylene, heptamethylene, octamethylene and isomers thereof.

In the formula (I), C3–8 alkenylene represented by $A^2$ means 1-propynylene, 1-butenylene, 2-butenylene, 2-methyl-2-butenylene, 3-methyl-2-butenylene, pentenylene, hexenylene, heptenylene, octenylene and isomers thereof.

In the formula (I), C3–8 alkynylene represented by $A^2$ means 1-propynylene, 1-butynylene, 2-butynylene, pentynylene, hexynylene, heptynylene, octynylene and isomers thereof.

In the formula (I), halogen represented by $R^1$ and $R^2$ or halogen as a substituent of carbocyclic ring or heterocyclic ring represented by $R^1$ means fluoride, chloride, bromide and iodide.

In the formula (I), C3–7 cycloalkylene represented by $R^3$ and $R^4$ taken together with carbon atom to which is attached means cycloheptylene, cyclobutylene, cyclopentylene, cyclohexylene and cycloheptylene.

In the formula (I), heterocyclic ring which is equivalent to the carboxylic acid represented by $R^5$ includes, for example, 1H-tetrazol-5yl, thiazolidine-2,4-dion-5-yl, oxazolidin-2,4-dion-5-yl, isooxazolidin-3,5-dion-4-yl, 1,2,4-oxadiazolidin-3,5-dion-2-yl etc. shown by the following structure:

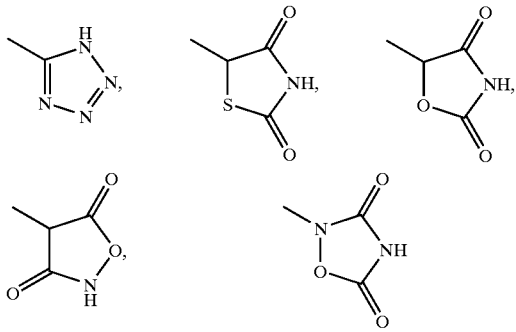

but does not limit to the said group.

In the formula (I), carbocyclic ring represented by $R^1$,

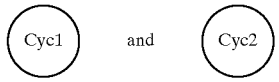

means C3–10 mono- or bi-cyclic carbocyclic ring and bicyclo carbocyclic ring. For example, C3–10 mono- or bi-cyclic carbocyclic ring and bicyclo carbocyclic ring mean cyclopropane, cyclobutane, cyclopentane, cyclohexane, cycloheptane, cyclooctane, cyclononane, cyclodecane, cyclopentene, cyclohexene, cyclopentadien, cyclohexadien, benzene, pentalene, indene, naphthalene, azulene, dihydronaphthalene, tetrahydronaphthalene, perhydronaphthalene, indane (dihydroindene), perhydroindene, bicyclopentane, bicyclohexane, bicycloheptane ([2.2.1]bicycloheptane), bicyclooctane, bicyclononane, bicyclodecane, adamantane etc.

In the formula (I), heterocyclic ring represented by $R^1$,

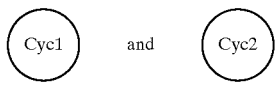

means 5–15-membered mono- or bi-cyclic heterocyclic ring containing 1–3 nitrogen atom(s), 1–2 oxygen atom(s) and/or one sulfur atom which is unsaturated or saturated partially or fully, For example, 5–15-membered mono- or bi-cyclic heterocyclic ring containing 1–3 nitrogen atom(s), 1–2 oxygen atom(s) and/or one sulfur atom which is unsaturated or saturated partially or fully includes pyroline, pyrrolidine, imidazoline, imidazolidine, pyrazoline, piperazolidine, piperidine, piperazine, tetrahydropyrimidine, hexahydropyrimidine, tetrahydropyridazine, hexahydropyridazine, hexahydroazepine, dihydrofuran, tetrahydrofuran, dihydropyran, tetrahydropyran, dihydrothiophene, tetrahydrothiophene, dihydrothiain (dihydrothiopyran), tetrahydrothiain (tetrahydrothi opyran), dihydroozazole, tetrahydroozazole, dihydroisooxazole, tetrahydroisooxazole, dihydrothiazole, tetrahydrothiazole, dihydroisothiazole, tetraisothiazole, morpholine, thiomorpholine, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthylidine, tetrahydronaphthylidine, perhydronaphthylidine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzooxazole, perhydrobenzooxazole, dihydrobenzothiazole, perhydrobenzothiazole, dihydrobenzoimidazole, perhydrobenzoimidazole, dihydrobenzooxazine, dioxaindane (1,3-dioxaindane), benzodioxane, quinuclidine, pyrrole, imidazole, pyrazole, pyridine, pyrazine, pyrimidine, pyridazine, pyridazine, azepine, diazepine, furan, pyran, oxepine, oxazepine, thiophene, thiain (thiopyran), thiepine, oxazole, isooxazole, thiazole, isothiazole, oxadiazole, oxazine, oxadiazine, oxazepine, oxadiazepine, thiadiazole, thiazine, thiadiazine, thiaazepine, thiaazepine, thiadiazepine, indole, isoindole, benzofuran, isobenzofuran, benzothiophene, isobenzothiophene, indazole, quinoline, isoquinoline, phthalazine, naphthylidine, quinoxaline, quinazoline, cinnoline, benzooxazole, benzothiazole, benzoimidazole, oxatetrahydrofuran, imidazopyridine, benzotriazole etc.

In the formula (I), $A^1$ is preferably, every group and more preferably methylene or ethylene.

In the formula (I), $A^2$ is preferably, every group, more preferably C4–6 alkylene, C4–6 alkenylene, C4–6 alkynylene, much more preferably tetramethylene 2-butenylene, 2-butynylene, or the said group which is substituted with 1–2 of methyl, and most preferably 2-butynylene.

In the formula (I), $E^1$ is preferably, every group and more preferably —O—.

In the formula (I), $E^2$ is preferably, every group and more preferably —S— or —CH$_2$—.

In the formula (I), $R^5$ is preferably, every group, more preferably —COOR$^9$, 1-tetrazol-5-yl, or thiazolidine-2,4-dion-5-yl and most preferably —COOR$^9$.

In the formula (I),

is preferably, every group, more preferably C5–6 mono-cyclic carbocyclic ring, or 5–6-membered mono-cyclic heterocyclic ring containing 1–2 nitrogen atom(s), one oxygen atom and/or one sulfur atom, much more preferably

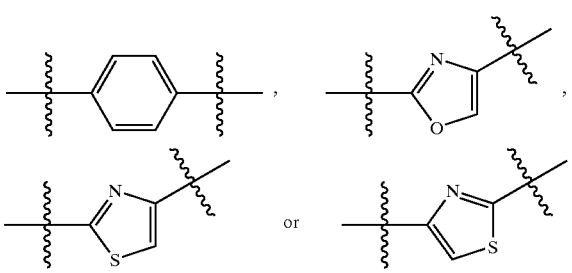

and most preferably

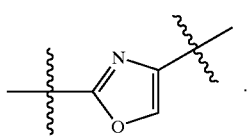

In the formula (I),

is preferably, every group, more preferably C5–10 mono- or bi-cyclic carbocyclic ring, or 5–1 0-membered mono- or bi-cyclic heterocyclic ring containing 1–2 nitrogen atom(s), 1–2 oxygen atom(s) and/or one sulfur atom which is unsaturated or saturated partially or fully, and most preferably cyclopentane, cyclohexane, cycloheptane, benzene, furan, thiophene, pyridine, quinoline, dioxaindane (for example, 1,3-dioxaindane).

In the present invention, PPAR regulator includes all the regulators of PPARα, γ, δ, α+γ, α+δ and α+γ+δ. Preferable regulatory fashion is, PPARα regulator, PPARγ regulator, PPARδ regulator, PPARα+γ regulator, PPARα+δ regulator, more preferably PPARα+γ regulator.

PPAR regulator also includes PPAR agonist and PPAR antagonist, preferably PPAR agonist, more preferably PPARα agonist, PPARγ agonist, PPARδ agonist, PPARα+γ agonist or PPARα+δ agonist, particularly preferably PPARα+γ agonist.

Among the compounds of the formula (I), compounds of the formula (Ia)

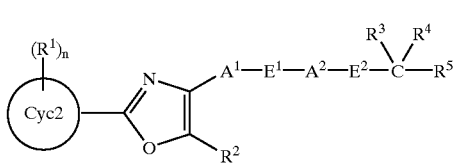

(Ia)

(wherein, all the symbols are the same meanings as defined hereinbefore), compounds of the formula (Ib)

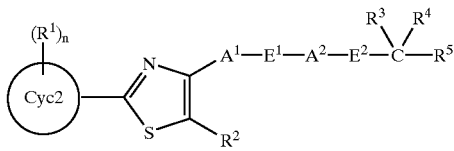

(Ib)

(wherein, all the symbols are the same meanings as defined hereinbefore), compounds of the formula (Ic)

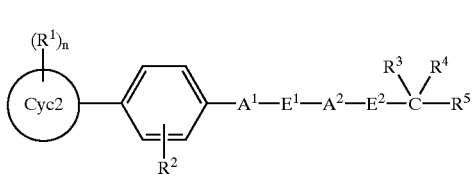

(Ic)

(wherein, all the symbols are the same meanings as defined hereinbefore), non-toxic salt thereof, or hydrate thereof are preferable.

The compounds of the formula (Ia-A)

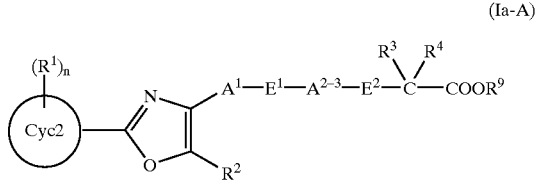

(Ia-A)

(wherein, $A^{2-3}$ is C3–8 alkynylene and the other symbols are the same meanings as defined hereinbefore), compounds of the formula (Ia-B)

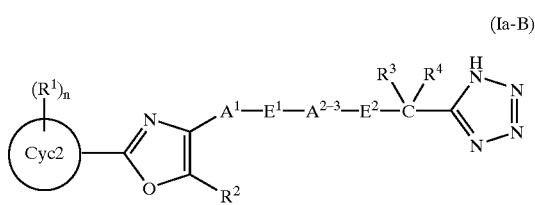

(Ia-B)

(wherein, all the symbols are the same meanings as defined hereinbefore), compounds of the formula (Ia-C)

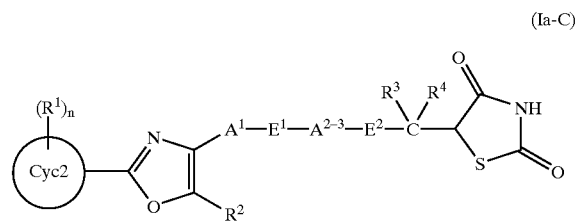

(Ia-C)

(wherein, all the symbols are the same meanings as defined hereinbefore), compounds of the formula (Ib-A)

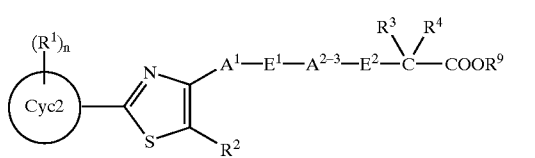

(Ib-A)

(wherein, all the symbols are the same meanings as defined hereinbefore), compounds of the formula (Ib-B)

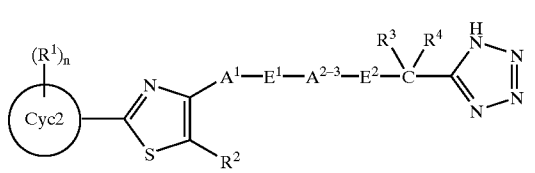

(Ib-B)

(wherein, all the symbols are the same meanings as defined hereinbefore), compounds of the formula (Ib-C)

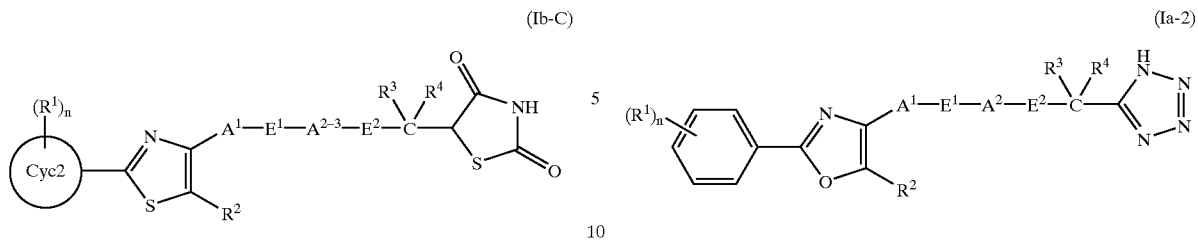

(wherein, all the symbols are the same meanings as defined hereinbefore), compounds of the formula (Ic-A)

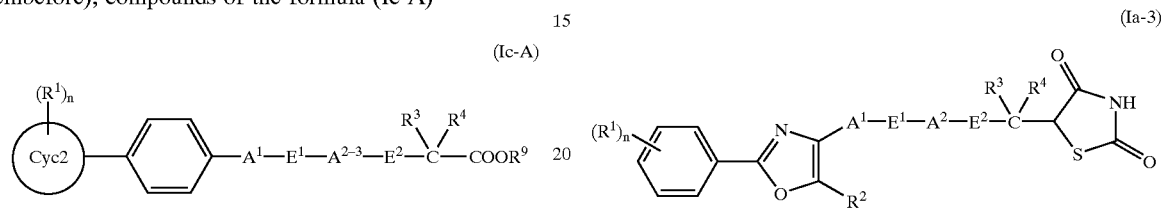

(wherein, all the symbols are the same meanings as defined hereinbefore), compounds of the formula (Ic-B)

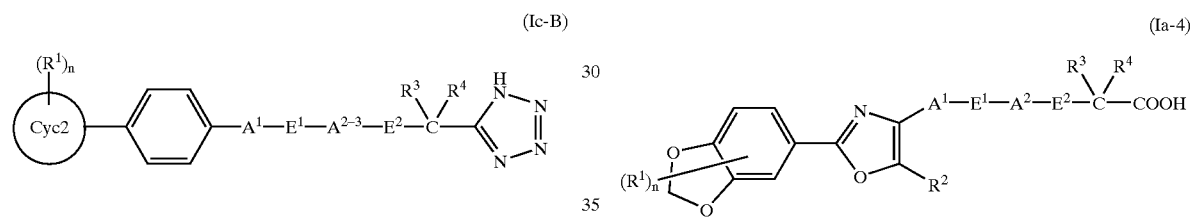

(wherein, all the symbols are the same meanings as defined hereinbefore), compounds of the formula (Ic-C)

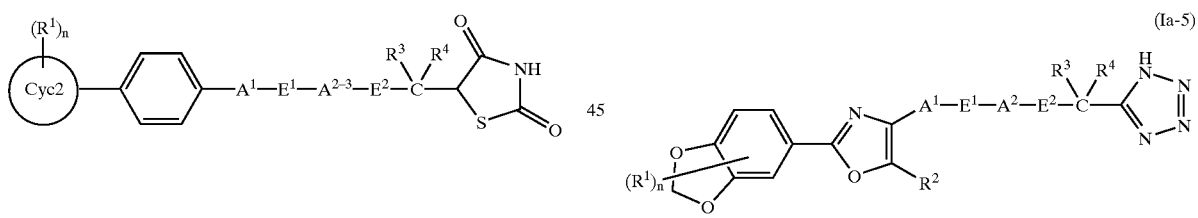

(wherein, all the symbols are the same meanings as defined hereinbefore), non-toxic salt thereof, or hydrate thereof are more preferable.

The compounds of the formula (Ia-1)

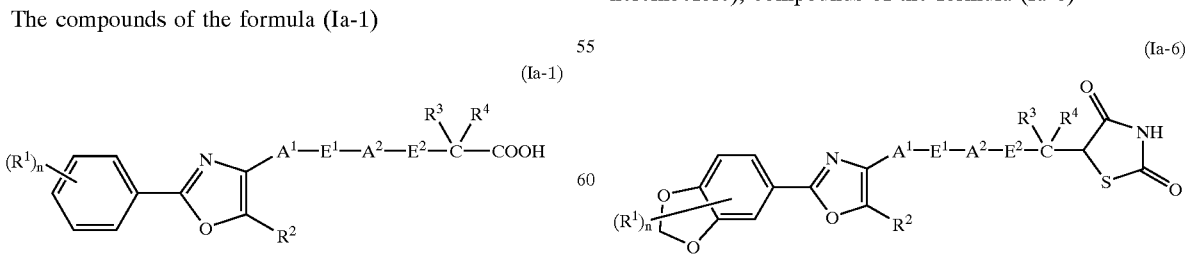

(wherein, all the symbols are the same meanings as defined hereinbefore), compounds of the formula (Ia-2)

(wherein, all the symbols are the same meanings as defined hereinbefore), compounds of the formula (Ia-3)

(wherein, all the symbols are the same meanings as defined hereinbefore), compounds of the formula (Ia-4)

(wherein, all the symbols are the same meanings as defined hereinbefore), compounds of the formula (Ia-5)

(wherein, all the symbols are the same meanings as defined hereinbefore), compounds of the formula (Ia-6)

(wherein, all the symbols are the same meanings as defined hereinbefore), compounds of the formula (Ib-1)

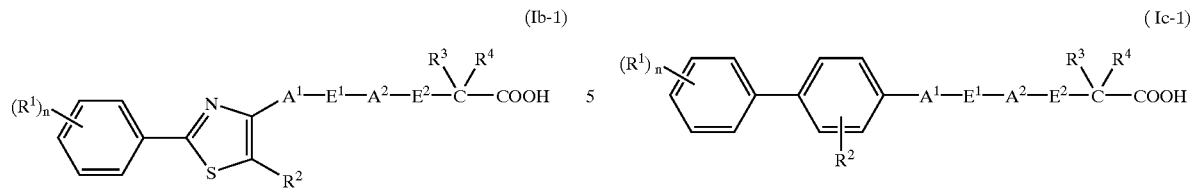

(wherein, all the symbols are the same meanings as defined hereinbefore), compounds of the formula (Ib-2)

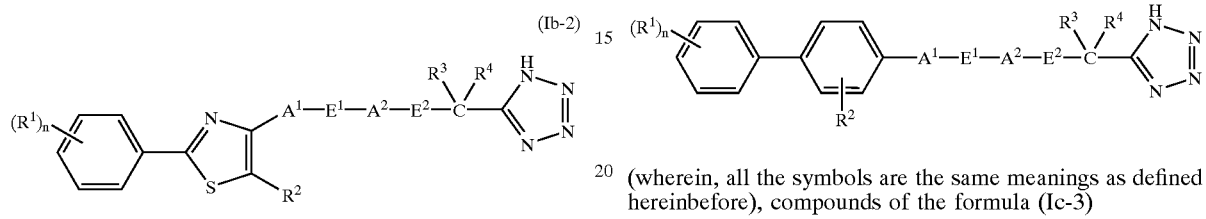

(wherein, all the symbols are the same meanings as defined hereinbefore), compounds of the formula (Ib-3)

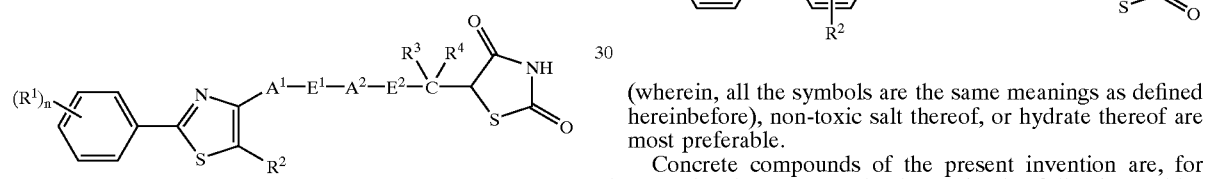

(wherein, all the symbols are the same meanings as defined hereinbefore), compounds of the formula (Ic-1)

(wherein, all the symbols are the same meanings as defined hereinbefore), compounds of the formula (Ic-2)

(wherein, all the symbols are the same meanings as defined hereinbefore), compounds of the formula (Ic-3)

(wherein, all the symbols are the same meanings as defined hereinbefore), non-toxic salt thereof, or hydrate thereof are most preferable.

Concrete compounds of the present invention are, for example, the compounds shown in the following Tables 1–16, non-toxic salts thereof and hydrates thereof, and compounds described in Example hereafter.

In each Table, Me is methyl and the other symbols are the same meanings as defined hereinbefore.

TABLE 1

(Ia-1-1)

| No. | $R^1$ | $A^2$ |
|---|---|---|
| 1 | H | ∿∿ |
| 2 | Me | ∿∿ |
| 3 | F | ∿∿ |
| 4 | Cl | ∿∿ |
| 5 | $CF_3$ | ∿∿ |
| 6 | OMe | ∿∿ |
| 7 | $NO_2$ | ∿∿ |

TABLE 1-continued (Ia-1-1)

R¹—⟨phenyl⟩—⟨oxazole with CH₃⟩—CH₂CH₂—O—A²—S—CH₂—COOH

| No. | R¹ | A² |
|-----|-----|-----|
| 8 | H | –CH₂–CH=CH–CH₂– |
| 9 | Me | –CH₂–CH=CH–CH₂– |
| 10 | F | –CH₂–CH=CH–CH₂– |
| 11 | Cl | –CH₂–CH=CH–CH₂– |
| 12 | CF₃ | –CH₂–CH=CH–CH₂– |
| 13 | OMe | –CH₂–CH=CH–CH₂– |
| 14 | NO₂ | –CH₂–CH=CH–CH₂– |
| 15 | H | –CH₂–C≡C–CH₂– |
| 16 | Me | –CH₂–C≡C–CH₂– |
| 17 | F | –CH₂–C≡C–CH₂– |
| 18 | Cl | –CH₂–C≡C–CH₂– |
| 19 | CF₃ | –CH₂–C≡C–CH₂– |
| 20 | OMe | –CH₂–C≡C–CH₂– |
| 21 | NO₂ | –CH₂–C≡C–CH₂– |

TABLE 2
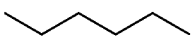
(Ia-1-2)
| No. | R¹ | A² |
|---|---|---|
| 1 | H | 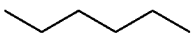 |
| 2 | Me | 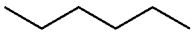 |
| 3 | F | 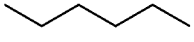 |
| 4 | Cl | 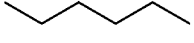 |
| 5 | CF₃ | 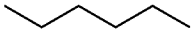 |
| 6 | OMe | 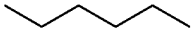 |
| 7 | NO₂ | 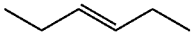 |
| 8 | H | 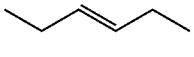 |
| 9 | Me | 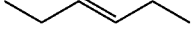 |
| 10 | F | 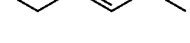 |
| 11 | Cl |  |
| 12 | CF₃ |  |
| 13 | OMe |  |
| 14 | NO₂ |  |
| 15 | H | 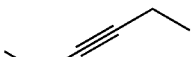 |
| 16 | Me |  |
| 17 | F |  |
| 18 | Cl | 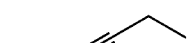 |
| 19 | CF₃ |  |
| 20 | OMe | |

TABLE 2-continued
(Ia-1-2)
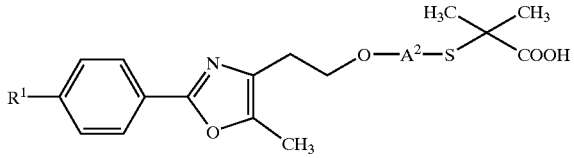
| No. | R¹ | A² |
|---|---|---|
| 21 | NO$_2$ | 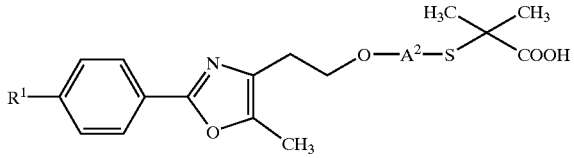 |
TABLE 3
(Ia-2-1)
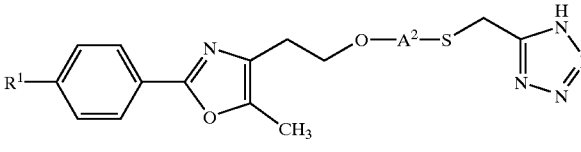
| No. | R¹ | A² |
|---|---|---|
| 1 | H | 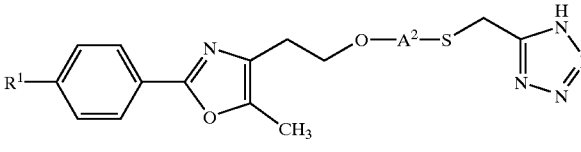 |
| 2 | Me | 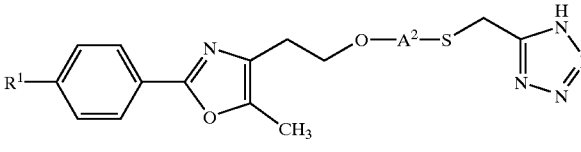 |
| 3 | F | 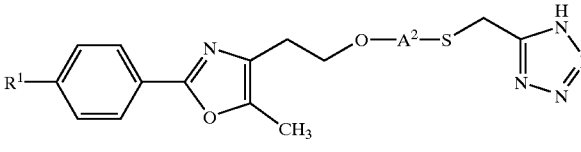 |
| 4 | Cl | 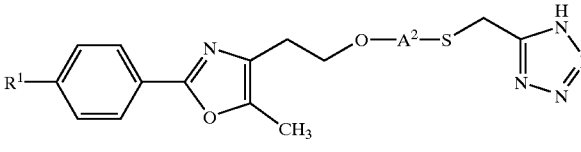 |
| 5 | CF$_3$ | 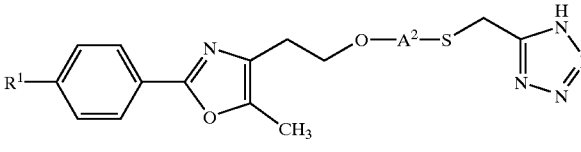 |
| 6 | OMe | 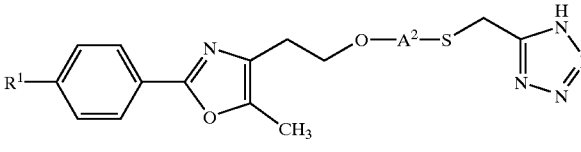 |
| 7 | NO$_2$ | 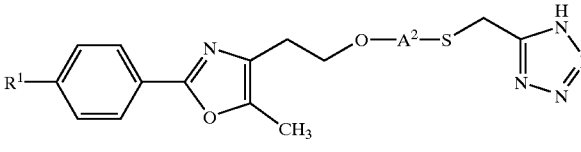 |
| 8 | H | 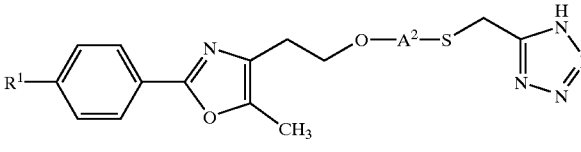 |
| 9 | Me | 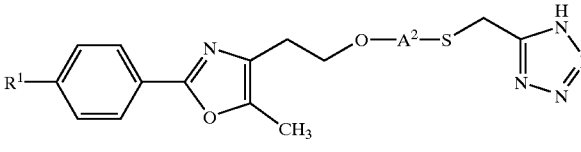 |
| 10 | F | 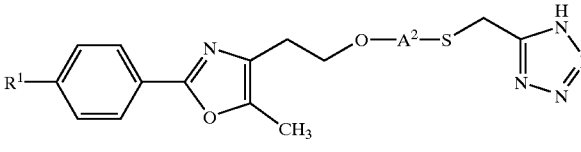 |
| 11 | Cl | 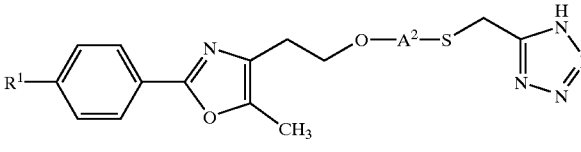 |
| 12 | CF$_3$ | 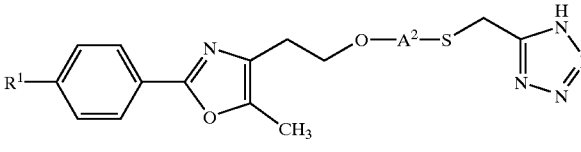 |
| 13 | OMe | 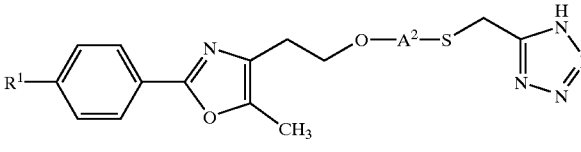 |
| 14 | NO$_2$ | 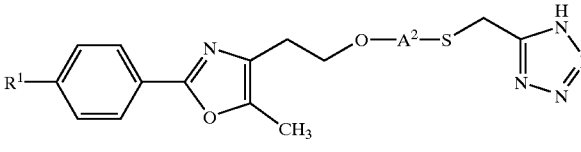 |
| 15 | H | 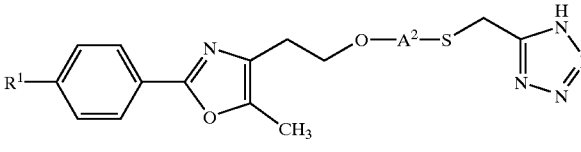 |

TABLE 3-continued (Ia-2-1)

| No. | R¹ | A² |
|---|---|---|
| 16 | Me | —CH₂—C≡C—CH₂CH₃ |
| 17 | F | —CH₂—C≡C—CH₂CH₃ |
| 18 | Cl | —CH₂—C≡C—CH₂CH₃ |
| 19 | CF₃ | —CH₂—C≡C—CH₂CH₃ |
| 20 | OMe | —CH₂—C≡C—CH₂CH₃ |
| 21 | NO₂ | —CH₂—C≡C—CH₂CH₃ |

TABLE 4

(Ia-3-1)

| No. | R¹ | A² |
|---|---|---|
| 1 | H | —(CH₂)₄— |
| 2 | Me | —(CH₂)₄— |
| 3 | F | —(CH₂)₄— |
| 4 | Cl | —(CH₂)₄— |
| 5 | CF₃ | —(CH₂)₄— |
| 6 | OMe | —(CH₂)₄— |
| 7 | NO₂ | —(CH₂)₄— |
| 8 | H | —CH₂—CH=CH—CH₂— |

TABLE 4-continued (Ia-3-1)

| No. | R¹ | A² |
| --- | --- | --- |
| 9 | Me | –CH₂–CH=CH–CH₃ |
| 10 | F | –CH₂–CH=CH–CH₃ |
| 11 | Cl | –CH₂–CH=CH–CH₃ |
| 12 | CF₃ | –CH₂–CH=CH–CH₃ |
| 13 | OMe | –CH₂–CH=CH–CH₃ |
| 14 | NO₂ | –CH₂–CH=CH–CH₃ |
| 15 | H | –CH₂–C≡C–CH₃ |
| 16 | Me | –CH₂–C≡C–CH₃ |
| 17 | F | –CH₂–C≡C–CH₃ |
| 18 | Cl | –CH₂–C≡C–CH₃ |
| 19 | CF₃ | –CH₂–C≡C–CH₃ |
| 20 | OMe | –CH₂–C≡C–CH₃ |
| 21 | NO₂ | –CH₂–C≡C–CH₃ |

TABLE 5

(Ia-4-1)

[Structure: benzo[1,3]dioxole-substituted oxazole with 5-methyl group, 4-position bearing -CH2CH2-O-A²-S-CH2-COOH; aryl ring substituents (R¹)ₙ]

| No. | (R¹)ₙ | A² |
|---|---|---|
| 1 | H | –CH₂CH₂CH₂CH₂CH₂– (pentylene) |
| 2 | 4-Me | pentylene |
| 3 | 4-F | pentylene |
| 4 | 4-Cl | pentylene |
| 5 | 4-CF₃ | pentylene |
| 6 | 4-OMe | pentylene |
| 7 | 4-NO₂ | pentylene |
| 8 | 2,2-di-F | pentylene |
| 9 | H | –CH₂CH=CHCH₂CH₂– (pentenylene) |
| 10 | 4-Me | pentenylene |
| 11 | 4-F | pentenylene |
| 12 | 4-Cl | pentenylene |
| 13 | 4-CF₃ | pentenylene |
| 14 | 4-OMe | pentenylene |
| 15 | 4-NO₂ | pentenylene |
| 16 | 2,2-di-F | pentenylene |
| 17 | H | –CH₂C≡CCH₂CH₂– (pentynylene) |
| 18 | 4-Me | pentynylene |
| 19 | 4-F | pentynylene |
| 20 | 4-Cl | pentynylene |

TABLE 5-continued (Ia-4-1)

| No. | $(R^1)_n$ | $A^2$ |
|---|---|---|
| 21 | 4-CF$_3$ | (CH$_2$-C≡C-CH$_2$CH$_2$) |
| 22 | 4-OMe | (CH$_2$-C≡C-CH$_2$CH$_2$) |
| 23 | 4-NO$_2$ | (CH$_2$-C≡C-CH$_2$CH$_2$) |
| 24 | 2,2-di-F | (CH$_2$-C≡C-CH$_2$CH$_2$) |

TABLE 6

(Ia-4-2)

| No. | $(R^1)_n$ | $A^2$ |
|---|---|---|
| 1 | H | (pentylene) |
| 2 | 4-Me | (pentylene) |
| 3 | 4-F | (pentylene) |
| 4 | 4-Cl | (pentylene) |
| 5 | 4-CF$_3$ | (pentylene) |
| 6 | 4-OMe | (pentylene) |
| 7 | 4-NO$_2$ | (pentylene) |
| 8 | 2,2-di-F | (pentylene) |
| 9 | H | (pentenylene) |
| 10 | 4-Me | (pentenylene) |
| 11 | 4-F | (pentenylene) |

TABLE 6-continued (Ia-4-2)

| No. | (R¹)ₙ | A² |
|---|---|---|
| 12 | 4-Cl | -CH₂-CH=CH-CH₂- |
| 13 | 4-CF₃ | -CH₂-CH=CH-CH₂- |
| 14 | 4-OMe | -CH₂-CH=CH-CH₂- |
| 15 | 4-NO₂ | -CH₂-CH=CH-CH₂- |
| 16 | 2,2-di-F | -CH₂-CH=CH-CH₂- |
| 17 | H | -CH₂-C≡C-CH₂- |
| 18 | 4-Me | -CH₂-C≡C-CH₂- |
| 19 | 4-F | -CH₂-C≡C-CH₂- |
| 20 | 4-Cl | -CH₂-C≡C-CH₂- |
| 21 | 4-CF₃ | -CH₂-C≡C-CH₂- |
| 22 | 4-OMe | -CH₂-C≡C-CH₂- |
| 23 | 4-NO₂ | -CH₂-C≡C-CH₂- |
| 24 | 2,2-di-F | -CH₂-C≡C-CH₂- |

TABLE 7

(Ia-5-1)

[Structure: benzodioxole-oxazole with -O-A²-S-CH₂-tetrazole substituent; oxazole bears CH₃ and (R¹)ₙ on the phenyl ring]

| No. | (R¹)ₙ | A² |
|---|---|---|
| 1 | H | -(CH₂)₆- (hexyl chain) |
| 2 | 4-Me | -(CH₂)₆- |
| 3 | 4-F | -(CH₂)₆- |
| 4 | 4-Cl | -(CH₂)₆- |
| 5 | 4-CF₃ | -(CH₂)₆- |
| 6 | 4-OMe | -(CH₂)₆- |
| 7 | 4-NO₂ | -(CH₂)₆- |
| 8 | 2,2-di-F | -(CH₂)₆- |
| 9 | H | -CH₂CH=CHCH₂CH₂- (alkenyl) |
| 10 | 4-Me | alkenyl |
| 11 | 4-F | alkenyl |
| 12 | 4-Cl | alkenyl |
| 13 | 4-CF₃ | alkenyl |
| 14 | 4-OMe | alkenyl |
| 15 | 4-NO₂ | alkenyl |
| 16 | 2,2-di-F | alkenyl |
| 17 | H | -CH₂C≡CCH₂CH₂- (alkynyl) |
| 18 | 4-Me | alkynyl |
| 19 | 4-F | alkynyl |
| 20 | 4-Cl | alkynyl |

TABLE 7-continued (Ia-5-1)

| No. | (R¹)ₙ | A² |
|---|---|---|
| 21 | 4-CF₃ | |
| 22 | 4-OMe | |
| 23 | 4-NO₂ | |
| 24 | 2,2-di-F | |

TABLE 8

(Ia-6-1)

| No. | (R¹)ₙ | A² |
|---|---|---|
| 1 | H | |
| 2 | 4-Me | |
| 3 | 4-F | |
| 4 | 4-Cl | |
| 5 | 4-CF₃ | |
| 6 | 4-OMe | |
| 7 | 4-NO₂ | |
| 8 | 2,2-di-F | |
| 9 | H | |
| 10 | 4-Me | |
| 11 | 4-F | |

TABLE 8-continued (Ia-6-1)

| No. | $(R^1)_n$ | $A^2$ |
|---|---|---|
| 12 | 4-Cl | –CH$_2$–CH=CH– |
| 13 | 4-CF$_3$ | –CH$_2$–CH=CH– |
| 14 | 4-OMe | –CH$_2$–CH=CH– |
| 15 | 4-NO$_2$ | –CH$_2$–CH=CH– |
| 16 | 2,2-di-F | –CH$_2$–CH=CH– |
| 17 | H | –CH$_2$–C≡C– |
| 18 | 4-Me | –CH$_2$–C≡C– |
| 19 | 4-F | –CH$_2$–C≡C– |
| 20 | 4-Cl | –CH$_2$–C≡C– |
| 21 | 4-CF$_3$ | –CH$_2$–C≡C– |
| 22 | 4-OMe | –CH$_2$–C≡C– |
| 23 | 4-NO$_2$ | –CH$_2$–C≡C– |
| 24 | 2,2-di-F | –CH$_2$–C≡C– |

TABLE 9

(Ib-1-1)

[Structure: R¹-phenyl-thiazole(5-CH₃)-CH₂CH₂-O-A²-S-CH₂-COOH]

| No. | R¹ | A² |
|---|---|---|
| 1 | H | (CH₂)₆ |
| 2 | Me | (CH₂)₆ |
| 3 | F | (CH₂)₆ |
| 4 | Cl | (CH₂)₆ |
| 5 | CF₃ | (CH₂)₆ |
| 6 | OMe | (CH₂)₆ |
| 7 | NO₂ | (CH₂)₆ |
| 8 | H | CH₂CH=CHCH₂CH₂CH₂ |
| 9 | Me | CH₂CH=CHCH₂CH₂CH₂ |
| 10 | F | CH₂CH=CHCH₂CH₂CH₂ |
| 11 | Cl | CH₂CH=CHCH₂CH₂CH₂ |
| 12 | CF₃ | CH₂CH=CHCH₂CH₂CH₂ |
| 13 | OMe | CH₂CH=CHCH₂CH₂CH₂ |
| 14 | NO₂ | CH₂CH=CHCH₂CH₂CH₂ |
| 15 | H | CH₂C≡CCH₂CH₂CH₂ |
| 16 | Me | CH₂C≡CCH₂CH₂CH₂ |
| 17 | F | CH₂C≡CCH₂CH₂CH₂ |
| 18 | Cl | CH₂C≡CCH₂CH₂CH₂ |
| 19 | CF₃ | CH₂C≡CCH₂CH₂CH₂ |
| 20 | OMe | CH₂C≡CCH₂CH₂CH₂ |

TABLE 9-continued (Ib-1-1)

R¹—⟨phenyl⟩—⟨thiazole with CH₃⟩—CH₂CH₂—O—A²—S—CH₂—COOH

| No. | R¹ | A² |
|---|---|---|
| 21 | NO₂ | —CH₂C≡C—CH₂CH₃ |

TABLE 10

(Ib-1-2)

R¹—⟨phenyl⟩—⟨thiazole with CH₃⟩—CH₂CH₂—O—A²—S—C(CH₃)₂—COOH

| No. | R¹ | A² |
|---|---|---|
| 1 | H | (CH₂)₅ |
| 2 | Me | (CH₂)₅ |
| 3 | F | (CH₂)₅ |
| 4 | Cl | (CH₂)₅ |
| 5 | CF₃ | (CH₂)₅ |
| 6 | OMe | (CH₂)₅ |
| 7 | NO₂ | (CH₂)₅ |
| 8 | H | —CH₂CH=CHCH₂CH₂— |
| 9 | Me | —CH₂CH=CHCH₂CH₂— |
| 10 | F | —CH₂CH=CHCH₂CH₂— |
| 11 | Cl | —CH₂CH=CHCH₂CH₂— |
| 12 | CF₃ | —CH₂CH=CHCH₂CH₂— |
| 13 | OMe | —CH₂CH=CHCH₂CH₂— |
| 14 | NO₂ | —CH₂CH=CHCH₂CH₂— |
| 15 | H | —CH₂C≡C—CH₂CH₃ |
| 16 | Me | —CH₂C≡C—CH₂CH₃ |

TABLE 10-continued (Ib-1-2)

[Structure: R¹-phenyl-thiazole(5-CH₃)-CH₂CH₂-O-A²-S-C(CH₃)₂-COOH]

| No. | R¹ | A² |
| --- | --- | --- |
| 17 | F | (alkynyl) |
| 18 | Cl | (alkynyl) |
| 19 | CF₃ | (alkynyl) |
| 20 | OMe | (alkynyl) |
| 21 | NO₂ | (alkynyl) |

TABLE 11

(Ib-2-1)

[Structure: R¹-phenyl-thiazole(5-CH₃)-CH₂CH₂-O-A²-S-CH₂-tetrazole]

| No. | R¹ | A² |
| --- | --- | --- |
| 1 | H | (alkyl) |
| 2 | Me | (alkyl) |
| 3 | F | (alkyl) |
| 4 | Cl | (alkyl) |
| 5 | CF₃ | (alkyl) |
| 6 | OMe | (alkyl) |
| 7 | NO₂ | (alkyl) |
| 8 | H | (alkenyl) |
| 9 | Me | (alkenyl) |
| 10 | F | (alkenyl) |

TABLE 11-continued
(Ib-2-1)
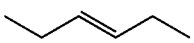
| No. | R¹ | A² |
|---|---|---|
| 11 | Cl | 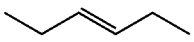 |
| 12 | CF₃ | 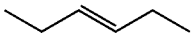 |
| 13 | OMe | 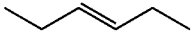 |
| 14 | NO₂ |  |
| 15 | H |  |
| 16 | Me |  |
| 17 | F |  |
| 18 | Cl |  |
| 19 | CF₃ |  |
| 20 | OMe |  |
| 21 | NO₂ | 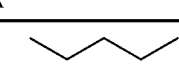 |
TABLE 12
(Ib-3-1)
| No. | R¹ | A² |
|---|---|---|
| 1 | H |  |
| 2 | Me |  |
| 3 | F |  |

TABLE 12-continued
(Ib-3-1)
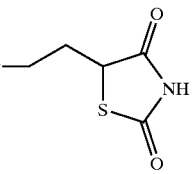
| No. | R¹ | A² | |
|---|---|---|---|
| 4 | Cl | 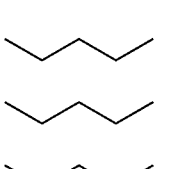 | |
| 5 | CF₃ | 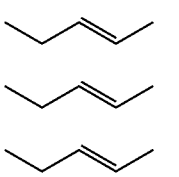 | |
| 6 | OMe | 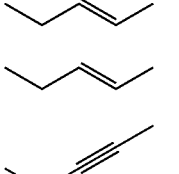 | |
| 7 | NO₂ | 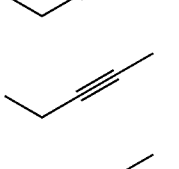 | |
| 8 | H | 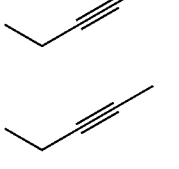 | |
| 9 | Me |  | |
| 10 | F | 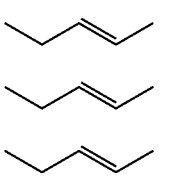 | |
| 11 | Cl | 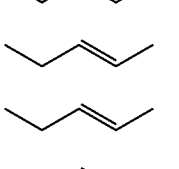 | |
| 12 | CF₃ | 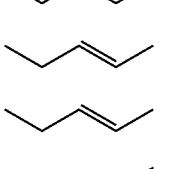 | |
| 13 | OMe | 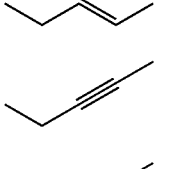 | |
| 14 | NO₂ | 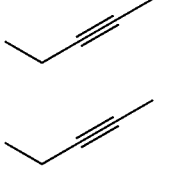 | |
| 15 | H | 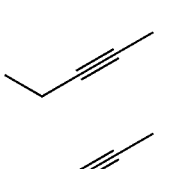 | |
| 16 | Me | 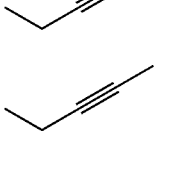 | |
| 17 | F | 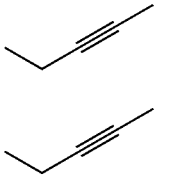 | |
| 18 | Cl |  | |
| 19 | CF₃ | | |
| 20 | OMe | | |
| 21 | NO₂ |  | |

TABLE 13

(Ic-1-1)

| No. | R¹ | A² |
|---|---|---|
| 1 | H | (hexyl chain) |
| 2 | Me | (hexyl chain) |
| 3 | F | (hexyl chain) |
| 4 | Cl | (hexyl chain) |
| 5 | CF₃ | (hexyl chain) |
| 6 | OMe | (hexyl chain) |
| 7 | NO₂ | (hexyl chain) |
| 8 | H | (hexenyl chain) |
| 9 | Me | (hexenyl chain) |
| 10 | F | (hexenyl chain) |
| 11 | Cl | (hexenyl chain) |
| 12 | CF₃ | (hexenyl chain) |
| 13 | OMe | (hexenyl chain) |
| 14 | NO₂ | (hexenyl chain) |
| 15 | H | (hexynyl chain) |
| 16 | Me | (hexynyl chain) |
| 17 | F | (hexynyl chain) |
| 18 | Cl | (hexynyl chain) |
| 19 | CF₃ | (hexynyl chain) |
| 20 | OMe | (hexynyl chain) |

TABLE 13-continued (Ic-1-1)

| No. | R¹ | A² |
|---|---|---|
| 21 | NO₂ | (hexynyl chain) |

TABLE 14

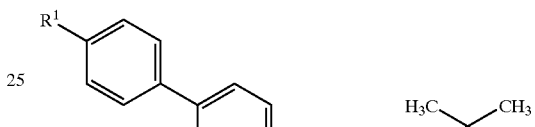

(Ic-1-2)

| No. | R¹ | A² |
|---|---|---|
| 1 | H | (hexyl chain) |
| 2 | Me | (hexyl chain) |
| 3 | F | (hexyl chain) |
| 4 | Cl | (hexyl chain) |
| 5 | CF₃ | (hexyl chain) |
| 6 | OMe | (hexyl chain) |
| 7 | NO₂ | (hexyl chain) |
| 8 | H | (hexenyl chain) |
| 9 | Me | (hexenyl chain) |
| 10 | F | (hexenyl chain) |
| 11 | Cl | (hexenyl chain) |
| 12 | CF₃ | (hexenyl chain) |
| 13 | OMe | (hexenyl chain) |
| 14 | NO₂ | (hexenyl chain) |
| 15 | H | (hexynyl chain) |

TABLE 14-continued
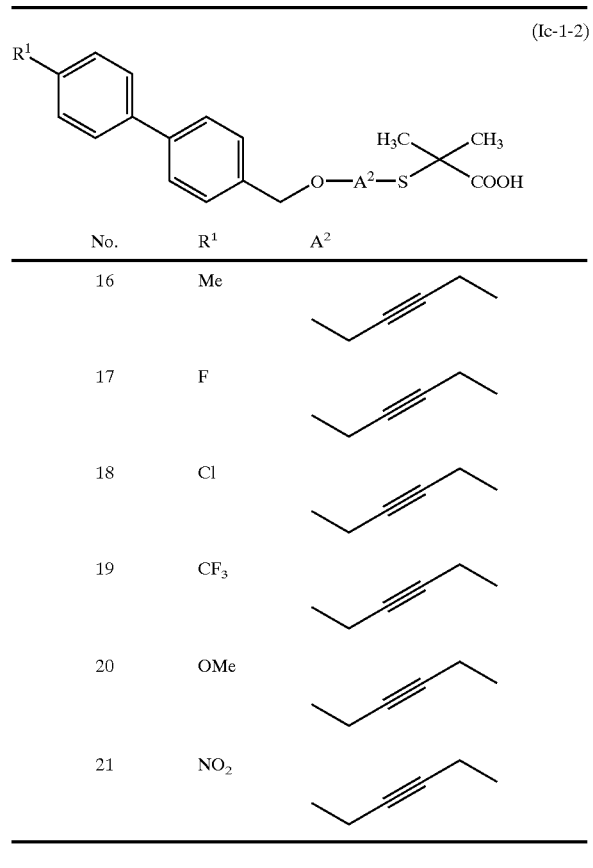
TABLE 15
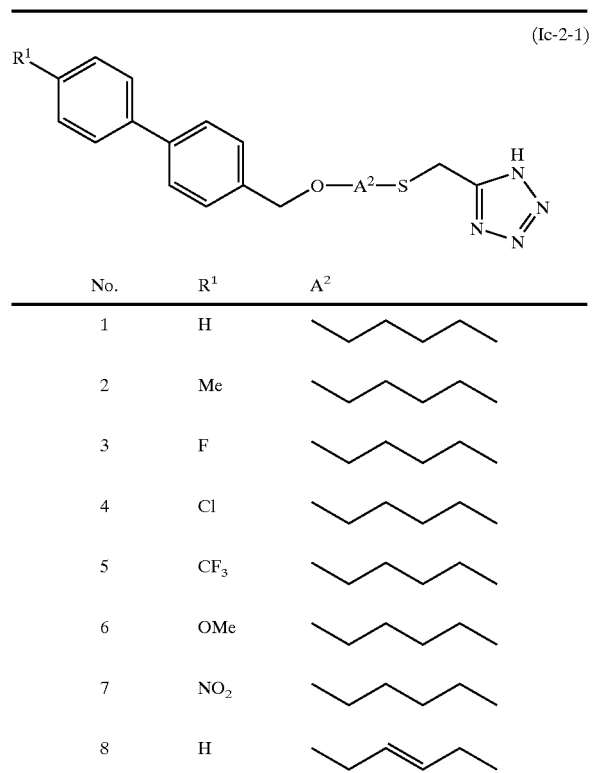
TABLE 15-continued
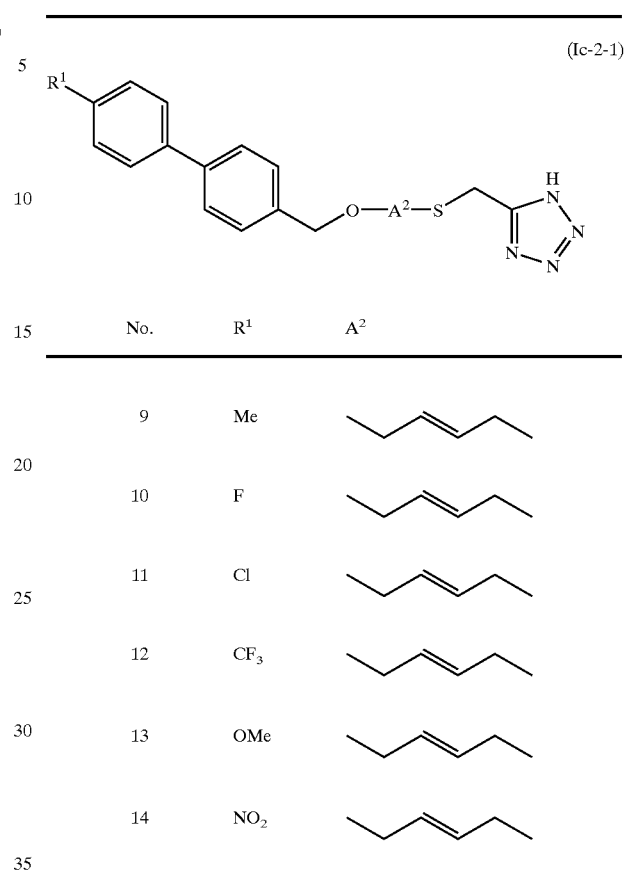
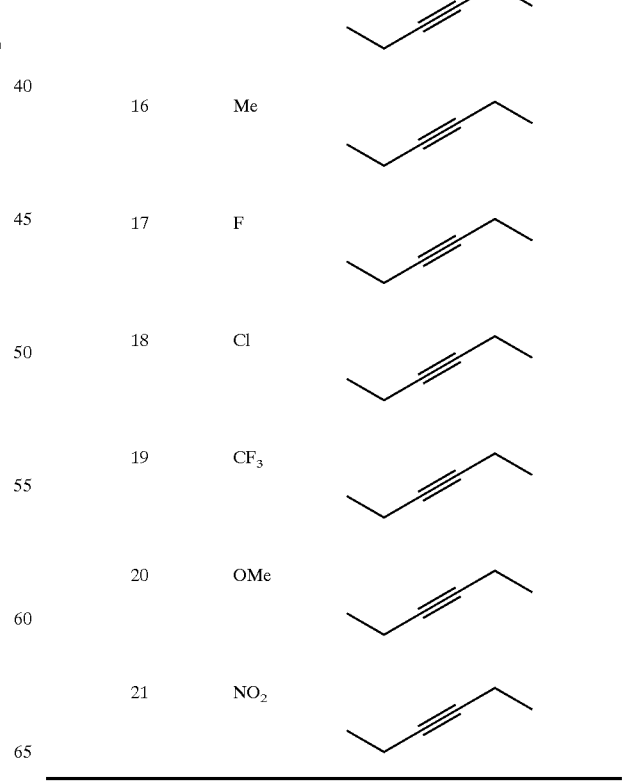

TABLE 16
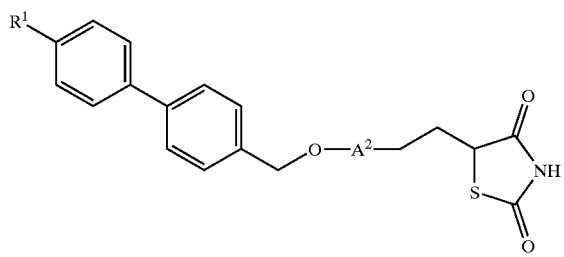
(Ic-3-1)
| No. | R¹ | A² |
|---|---|---|
| 1 | H | ~~~~~ |
| 2 | Me | ~~~~~ |
| 3 | F | ~~~~~ |
| 4 | Cl | ~~~~~ |
| 5 | $CF_3$ | ~~~~~ |
| 6 | OMe | ~~~~~ |
| 7 | $NO_2$ | ~~~~~ |
| 8 | H | ~~=~~ |
| 9 | Me | ~~=~~ |
| 10 | F | ~~=~~ |
| 11 | Cl | ~~=~~ |
| 12 | $CF_3$ | ~~=~~ |
| 13 | OMe | ~~=~~ |
| 14 | $NO_2$ | ~~=~~ |
| 15 | H | ~≡~ |
| 16 | Me | ~≡~ |
| 17 | F | ~≡~ |
| 18 | Cl | ~≡~ |
| 19 | $CF_3$ | ~≡~ |

TABLE 16-continued (Ic-3-1)

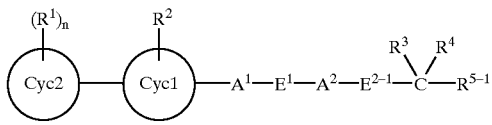

| No. | R¹ | A² |
|---|---|---|
| 20 | OMe | 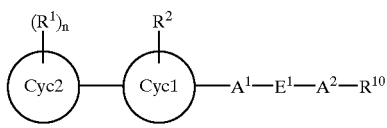 |
| 21 | NO$_2$ | 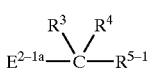 |

Process for Producing the Compounds of the Present Invention (a) Compounds of the formula (I) wherein $E^2$ is —O— or —S— and $R^5$ is —COOR$^{9-1}$ (in which $R^{9-1}$ is C1–4 alkyl) or heterocyclic ring which is equivalent to carboxylic acid, i.e., the compounds of the formula (I-A)

(I-A)

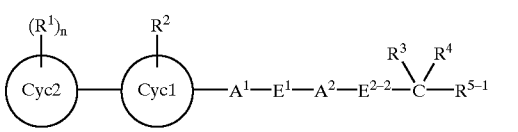

(wherein, $E^{2-1}$ is —O— or —S—, $R^{5-1}$ is —COOR$^{9-1}$ (in which $R^{9-1}$ is C1–4 alkyl) or heterocyclic ring which is equivalent to carboxylic acid and the other symbols are the same meanings as defined hereinbefore)
may be prepared by reacting the compounds of the formula (II)

(II)

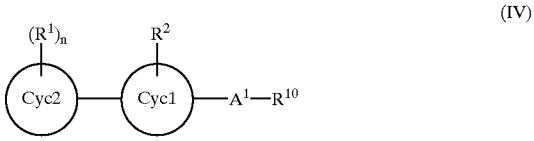

(wherein, $R^{10}$ is methanesulfonyloxy or halogen and the other symbols are the same meanings as defined hereinbefore) and the compounds of the formula (III)

(III)

(wherein, $E^{2-1a}$ is —OH or —SH and the other symbols are the same meanings as defined hereinbefore).

The said reaction may be carried out by known methods. It may be carried out, for example, in an organic solvent (tetrahydrofuran (THF), diethylether, methylene chloride, chloroform, tetrachloromethane, pentane, hexane, benzene, toluene, dimethylformamide (DMF), dimethylsulfoxide (DMSO), hexamethylphosphamide (HMPA), acetonitrile etc.) in the presence of base (sodium hydroxide, potassium carbonate, triethylamine, pyridine, sodium iodide, potassium iodide, cesium carbonate etc.) at 0–80° C.

(b) Compounds of the formula (I) wherein $E^2$ is —CH$_2$— and $R^5$ is —COOR$^{9-1}$ (in which $R^{9-1}$ is C1–4 alkyl) or heterocyclic ring which is equivalent to carboxylic acid, i.e., the compounds of the formula (I-B)

(I-B)

(wherein, $E^{2-2}$ is —CH$_2$— and the other symbols are the same meanings as defined hereinbefore)
may be prepared by reacting the compounds of the formula (IV)

(IV)

(wherein, all the symbols are the same meanings as defined hereinbefore) and the compounds of the formula (V-1)

(V-1)

(wherein, $E^{1-1}$ is —OH or —SH and the other symbols are the same meanings as defined hereinbefore) or by reacting the compounds of the formula (VII)

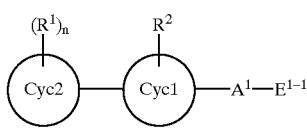

(VII)

(wherein, all the symbols are the same meanings as defined hereinbefore) and the compounds of the formula (V-2)

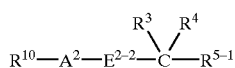

(V-2)

(wherein, all the symbols are the same meanings as defined hereinbefore).

The said reaction may be carried out by known methods. It may be carried out, for example, in an organic solvent (THF, diethylether, methylene chloride chloroform, tetrachloromethane, pentane, hexane, benzene, toluene, DMF, DMSO, HMPA, or mixture solvent thereof etc.) in the presence of base (sodium hydroxide, potassium carbonate, triethylamine, pyridine, sodium iodide, cesium carbonate etc.) at 0–80° C.

(c) Compounds of the formula (I) wherein $E^2$ is —O—, —S—, or —CH$_2$—and $R^5$ is —COOH, i.e., the compounds of the formula (I-C)

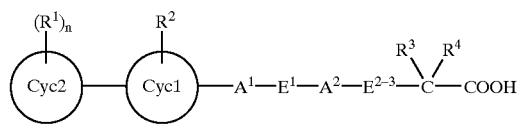

(I-C)

(wherein, $E^{2-3}$ is —O—, —S—, or —CH$_2$— and the other symbols are the same meanings as defined hereinbefore) may be prepared by hydrolysis of the compounds of the formula (I-A) wherein $R^{5-1}$ is —COOR$^{9-1}$, i.e., the compounds of the formula (I-A-1)

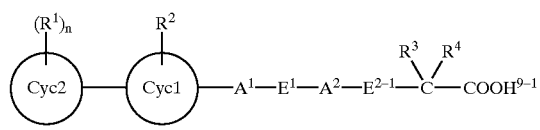

(I-A-1)

(wherein, all the symbols are the same meanings as defined hereinbefore) or the compounds of the formula (I-B) wherein $R^{5-1}$ is —COOR$^{9-1}$, i.e., the compounds of the formula (I-B-1)

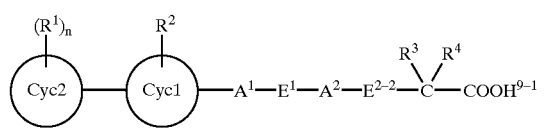

(I-B-1)

(wherein, all the symbols are the same meanings as defined hereinbefore).

In addition, compounds of the formula (I-C) wherein $A^2$ is C3–8 alkynylene and $E^2$ is —CH$_2$—, i.e., the compounds of the formula (I-C-1)

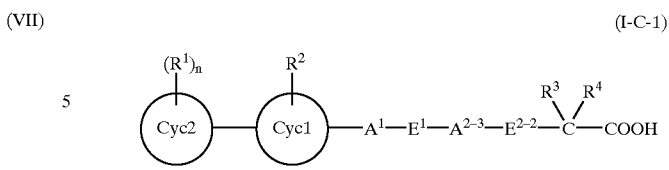

(I-C-1)

(wherein, $A^{2-3}$ is C3–8 alkynylene and the other symbols are the same meanings as defined hereinbefore)

may be prepared by hydrolysis of the compounds of the formula (XII)

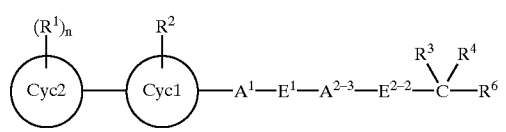

(XII)

(wherein, $R^6$ is a carboxyl group which is protected (for example, 4-methyl-2,6,7-trioxabicyclo[2,2,2]octan-1-yl etc.) and the other symbols are the same meanings as defined hereinbefore).

The said hydrolysis may be carried out by known methods. It may be carried out, for example, (1) in an organic solvent admissible with water (THF, dioxane, ethanol, methanol etc.) or mixture solvent thereof, using an aqueous solution of alkali (potassium hydroxide, sodium hydroxide, lithium hydroxide, potassium carbonate, sodium carbonate etc.), (2) in alkanol (methanol, ethanol etc.), using the above alkali under an anhydrous condition or (3) in an organic solvent (THF, dioxane, ethanol, methanol etc.) or mixture solvent thereof, using acid (hydrochloric acid, sulfuric acid etc.) and alkali (sodium hydroxide, potassium hydroxide etc.).

These reactions may be carried out at 0–100° C. normaly. In addition, the said hydrolysis may be carried out (4) in mixture solvent of an organic solvent admissible with water (ethanol, dimethylsulfoxide etc.) and water, in the presence or absence of buffer, using enzyme to decompose ester (esterase, lipase etc.) at 0–50° C.

(d) Compounds of the formula (I) wherein $E^2$ is —O—, —S— or —CH$_2$— and heterocyclic ring represented by $R^5$ which is equivalent to carboxylic acid is 1H-tetrazol-5-yl, i.e., the compounds of the formula (I-D)

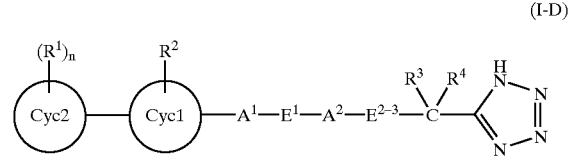

(I-D)

(wherein, all the symbols are the same meanings as defined hereinbefore) may be also prepared by reacting the compounds of the formula (VI)

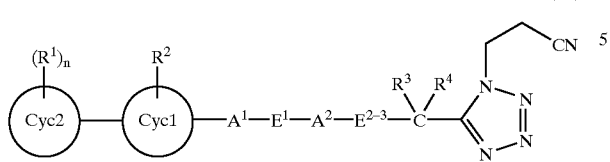

(VI)

(wherein, all the symbols are the same meanings as defined hereinbefore) in an alkaline condition.

The said reaction may be carried out by known methods. It may be carried out, for example, in an organic solvent admissible with water (methanol, ethanol, dioxane etc.), using alkali (potassium hydroxide, sodium hydroxide, potassium carbonate, sodium carbonate etc.) at 0–50° C.

(e) Compounds of the formula (I) wherein m is 1 or 2, that is to say, $E^2$ is —SO— or —SO$_2$—, i.e., the compounds of the formula (I-E)

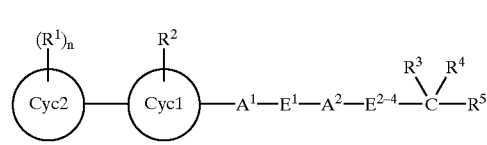

(I-E)

(wherein, $E^{2-4}$ is —S(O)$_{mm}$-(in which mm is 1 or 2) and the other symbols are the same meanings as defined hereinbefore)
may be prepared by oxidizing the compounds of the formula (I-A) wherein $E^{2-1}$ is —S— or the compounds of the formula (I-C) or (I-D) wherein each E 2-3 is —S—.

In addition, the compounds of the formula (I-E) wherein E 2-4 is —SO$_2$— may be also parepared by oxidizing the compounds of the formula (I-E) wherein $E^{2-4}$ is —SO—.

The said oxidizing may be carried out by known methods. It may be carried out, for example in an organic solvent (THF, methylene chloride, chloroform etc.), using a necessaryl amount of oxidizing agent (perhydrogen oxide, sodium periodate, acyl nitrite, sodium perboronate, peracid (e.g., 3-chloroperbenzoic acid, peracetic acid, OXONE (trade mark)) etc.) at 0–50° C.

The compounds of the formulae (II), (III), (IV), (V-1), (V-2), (VI), (VII) and (XII) are known per se or may be prepared by known methods.

For example, among the compounds of the formula (III), mercaptoacetic acid methyl ester (thioglycolic acid methyl) has been marketed.

For example, the compounds of the formulae (II), (IV), (VI) and (XII) may be prepared according to the following Reaction Schemes 1–4.

In each Reaction Scheme, the abbrevation and symbols are as the following meanings and the other symbols are the same meanings as defined hereinbefore.

THP: tetrahydropyran-2-yl,
$A^{2-1}$: C3–8 alkenylene or C3–8 alkynylene,
X: halogen,
$A^{2-2}$: C2–8 alkylene,
EDC HCl: 1-ethyl-3-(3-dimethylaminopropyl)-carbodiimide hydrochloride,
HOBt: 1-hydroxybenzotriazole,
Et$_3$N: triethylamine,
TMSN$_3$: trimethylsilylazide.

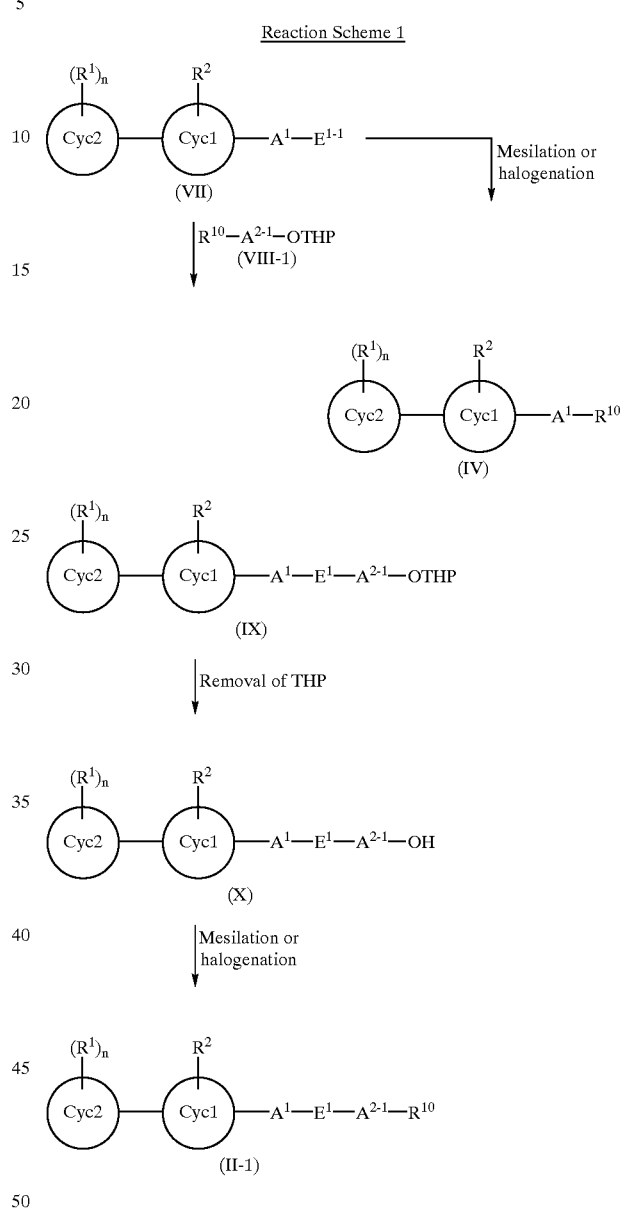

Reaction Scheme 1

Reaction Scheme 2

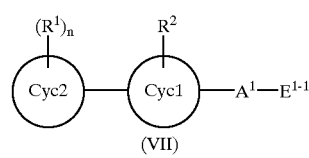

-continued

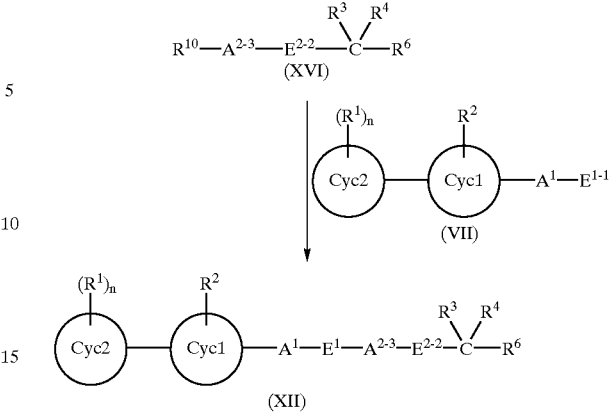

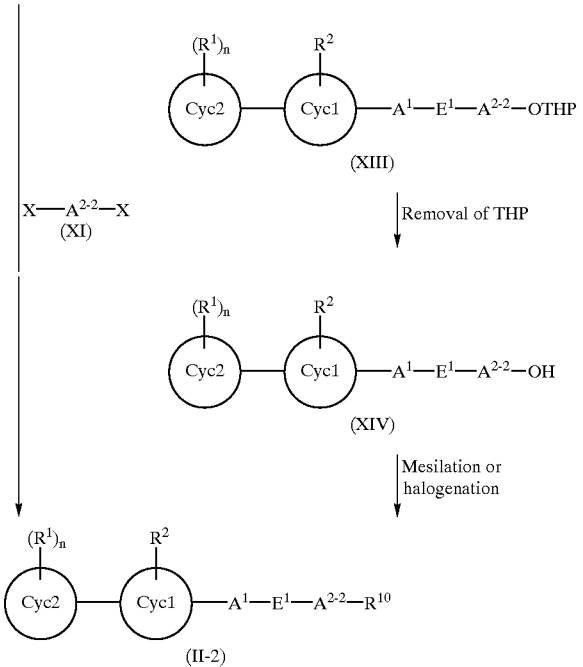

Reaction Scheme 3

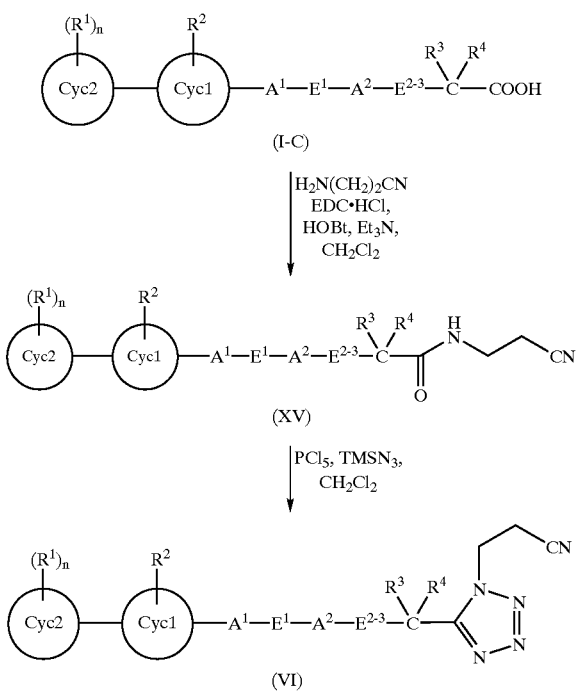

Reaction Scheme 4

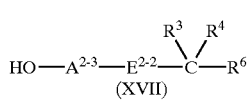

(XVII)

Mesilation or halogenation

In the said Reaction Schemes, the compounds of the formula (VII), (VIII-1), (VIII-2), (XI) and (XVII) are known per se or may be prepared by known methods.

The reactions described in the above-mentioned Schemes may be carried out by known methods.

In the present invention, the other starting materials and each reagent are known per se or may be prepared by known methods.

In each reaction in the present specification, products may be purified by a conventional manner. For example, it may be carried out by distillation at atmospheric or reduced pressure, high performance liquid chromatography, thin layer chromatography or column chromatography using silica gel or magnesium silicate, washing or recrystallization. Purification may be carried out after each reaction or after a series of reactions.

All the non-toxic salts are also included in the present invention. For example, the compounds of the formula (I) of the present invention may be converted into the corresponding salts by known methods. Non-toxic and water-soluble salts are preferable. Suitable salts, for example, are follows: salts of alkaline metals (potassium, sodium etc.), salts of alkaline earth metals (calcium, magnesium etc.), ammonium salts, salts of pharmaceutically acceptable organic amines (tetramethylammonium, triethylamine, methylamine, dimethylamine, cyclopentylamine, cyclohexylamine, benzylamine, phenethylamine, piperidine, monoethanolamine, diethanolamine, tris(hydroxymethyl)amine, lysine, arginine, N-methyl-D-glucamine etc.).

The compounds of the formula (I) of the present invention may be converted into the corresponding acid additional salts by methods known per se. Non-toxic and water-soluble acid addition salts are preferable. Suitable acid addition salts, for example, are salts of inorganic acids, e.g., hydrochloride, hydrobromide, sulphate, phosphate, nitrate etc., or salts of organic acids, e.g., acetate, trifluoroacetate, lactate, tartarate, oxalate, fumarate, maleate, citrate, benzoate, methanesulphonate, ethanesulphonate, benzenesulphonate, toluenesulphonate, isethioate, glucuronate, gluconate etc.

The compounds of the formula (I) of the present invention or salts thereof may be converted into hydrate thereof by methods known per se.

Pharmacological Activity

It was confirmed that a compound of the present invention of formula (I) has PPAR regulating activities by the following experiments.

Measurement of PPARα Agonistic and PPARγ Agonistic Activities (1) Preparation of Materials in Luciferase Assay Using Human PPARα or δ

The whole operations were carried out by the basic methods in gene engineering techniques and the conventional methods in yeast One-hybrid or Two-hybrid system.

As a luciferase gene expression vector under the control of thymidine kinase (TK) promotor, luciferase structural gene was exiced from PicaGene Basic Vector 2 (trade name, Toyo Ink Inc., catalogue No. 309-04821), to prepare luciferase gene expression vector pTK-Luc. under the control of TK promotor (−105/+51) as a minimum essential promotor activity from pTKβ having TK promotor (Chrontech Inc., catalogue No. 6179-1). In the upper stream of TK promotor, four times repeated UAS sequence was inserted, which is the response element of Gal4 protein, a basic transcription factor in yeast, to construct 4×UAS-TK-Luc. as reporter gene. The following is the enhancer sequence used (Sequence No. 1).

Sequence No. 1: Enhancer sequence repeating Gal4 response element four-times tandemly.

5'-T(CGACGGAGTACTGTCCTCCG)×4 AGCT-3'

A vector was prepared as described hereafter which expresses chimeric receptor protein wherein in carboxyl terminus of yeast Gal4 protein DNA binding domain was fused to ligand binding domain of human PPARα or γ. That is to say, PicaGene Basic Vector 2 (trade name, Toyo Ink Inc., catalogue No. 309-04821) was used as a basic expression vector, the structural gene was exchanged for that of chimeric receptor protein, while promotor and enhancer domains were kept as they were.

DNA encoding a fused protein composed of Gal4 DNA binding domain, the 1st to 147th amino acid sequence linked to the ligand binding domain of human PPARα or γ in frame was inserted to the downstream of promotor/enhancer in PicaGene Basic Vector 2 (trade name, Toyo Ink Inc., catalogue No. 309-04821). Here the DNA was aligned as follows; in the amino terminus of human PPARα or γ ligand binding domain, nuclear translocation signal originated from SV-40 T-antigen, Ala Pro Lys Lys Lys Arg Lys Val Gly (sequence No. 2) was added to make fusion protein localizing intranuclearly. On the other hand, in the carboxy terminus of them, influenza hemagglutinin epitope, Tyr Pro Tyr Asp Val Pro Asp Tyr Ala (sequence No. 3) and stop codon for translation was added in this order, to detect an expressed fused protein tagged epitope sequence.

According to the comparison of human PPAR structures described in the literature by R. Mukherjee at al. (See J. Steroid Biochem. Molec. Biol., 51, 157 (1994)), M. E. Green et al., (See Gene Expression., 4, 281 (1995)), A. Elbrecht et al. (See Biochem Biophys. Res. Commun., 224, 431 (1996)) or A. Schmidt et al. (See Mol. Endocrinology., 6, 1634 (1992)), the portion of structural gene used as ligand binding domain of human PPARα or γ was DNA encoding the following peptide:

human PPARα ligand binding domain: $Ser^{167}$-$Tyr^{468}$ human PPARγ ligand binding domain: $Ser^{176}$-$Tyr^{478}$ (each human PPARγ1 ligand binding domain and human PPARγ2 ligand binding domain is $Ser^{204}$-$Tyr^{506}$ which is identical sequence each other).

In order to measure basal level of transcription, an expression vector containing DNA binding domain of Gal4 protein lacking in PPAR ligand binding domain, which is exclusively encoding the 1st to 147th amino acid sequence in Gal4 protein was also prepared.

(2) Luciferase Assay Using Human PPARα or γ

CV-1 cells used as host cells were cultured by a conventional technique. That is to say, Dulbecco's modified Eagle medium (DMEM) supplemented 10% bovine fetal serum (GIBCO BRL Inc., catalogue No. 26140-061) and 50 U/ml of penicillin G and 50 μg/ml of streptomycin sulfate were used to culture CV-1 cells under the atmosphere of 5% carbon dioxide gas at 37° C.

$2 \times 10^6$ cells were seeded in a 10 cm dish, and once washed with the medium without serum, followed by addition of the medium (10 ml) thereto. Reporter gene (10 μg), Gal4-PPAR expression vector (0.5 μg) and 50 μg of LipofectAMINE (GIBRO BRL Inc., catalogue No. 18324-012) were well mixed and added to the culture to introduce these DNAs into the host cells. They were cultured at 37° C. for 5–6 hours, and thereto was added 10 ml of medium containing 20% of dialyzed bovine fetal serum (GIBRO BRL Inc., catalogue No. 26300-061), and then cultured at 37° C. overnight. The cells were dispersed by trypsin, and they were again seeded in 96-well plates in a density of 8000 cells/ 100 ml of DMEM-10% dialyzed serum/well. Several hours after the cultivation, when cells were attached to the plastic ware, then 100 μl of DMEM-10% dialyzed serum containing the compounds of the present invention, whose concentration is twice as high as the final concentration of them, was added thereto. The culture was settled at 37° C. for 42 hours and the cells were dissolved to measure luciferase activity according to manufacturer's instruction.

As to PPARα agonistic activity, the relative activity of the compounds of the present invention (10 μM) was shown in Table 17, under the condition that luciferase activity was defined as 1.0 in case of carbacyclin (10 μM) as a positive control compound, which could activate transcription of luciferase gene significantly to PPARα (See Eur. J. Biochem., 233, 242 (1996); Genes & Development., 10, 974 (1996)).

As to PPARγ agonistic activity, the relative activity of the compounds of the present invention (10 μM) was shown in Table 18, under the condition that luciferase activity was defined as 1.0 in case of troglitazone (10 μM) as a positive control compound, which could activate transcription of luciferase gene significantly to PPARγ (See Cell., 83, 863 (1995); Endocrinology., 137, 4189 (1996) and J. Med. Chem., 39, 665 (1996)) and has been already launched as hypoglycemic agent.

Furthermore, assay of each compound was carried out three times to examine its reproducibility and to confirm the dose dependent activity.

TABLE 17

| Example Nos. | Relative Activity to a positive control compound (carbacyclin = 1) |
|---|---|
| Example 5 | 2.8 |
| Example 5 (2) | 2.9 |
| Example 5 (8) | 2.2 |
| Example 5 (10) | 1.5 |
| Example 5 (11) | 1.7 |

TABLE 18

| Example Nos. | Relative Activity to a positive control compound (troglitazone = 1) |
|---|---|
| Example 5 | 2.6 |
| Example 5 (2) | 2.6 |
| Example 5 (8) | 2.3 |

TABLE 18-continued

| Example Nos. | Relative Activity to a positive control compound (troglitazone = 1) |
|---|---|
| Example 5 (10) | 2.7 |
| Example 5 (11) | 2.3 |

Hypoglycemic and Hypolipidemic Effects

Male, 7-weeks old KKAy/Ta mice weighed from 35 to 40 g (five mice per group) were pre-breaded for approximately one week and acclimatized for three days on milled diet. On the first day of the experiment (Day 0), mice were divided into some groups according to weight, plasma glucose and triglyceride (TG) levels to minimize the differences among groups. From the next day for two days they were given compounds by food mixture containing 0.03% (w/w) of the compound of the present invention or by milled diet only. At 13:00 of the third day, blood samples were collected to measure glucose and TG levels. The results are shown in Table 19. Additionally, there was no significant difference in the food intake between control group (milled diet only) and compounds-treated group (milled diet containing 0.03% compounds).

TABLE 19

| Example Nos. | glycemic level (mg/dl) on Day 3 | TG level (mg/dl) on Day 3 |
|---|---|---|
| Control | 638 ± 63 | 523 ± 144 |
| food containing compound of Example 5 (10) at 44.7 mg/kg/day (converted) | 339 ± 74* | 111 ± 38* |
| food containing compound of Example 5 (11) at 43.9 mg/kg/day (converted) | 306 ± 72* | 140 ± 75* |

*: $p < 0.01$ vs control (5 mice per group)

Hypocholesterolemic and Hypolipidemic Effects

Male, six-weeks old SD rats (five rats per group) were left to take milled diet and water ad libitum and were acclimatized for 1 week.

At 9:00 on the first day of the experiment (Day 0), blood sampling was done from tail vain. The rats were divided into some groups according to body weight, triglyceride (TG), non-esterified fatty acid (NEFA) and total cholesterol (TC) levels to minimize differences of the parameters among the groups. At 17:00 of the day, the compound of the present invention dissolved in 0.5% aqueous solution of carboxymethylcellulose (CMC) was orally administered, and thereafter, with hypercholesterolemic food (5.5% peanut oil, 1.5% cholesterol and 0.5% cholic acid were mixed with milled CRF-1 diet, Charles River Inc.) was given to the rats.

At 9:00 of the next day, blood sampling was done from tail vein. The lipid levels in blood (TG, NEFA and TC levels) after administration of the compounds of the present invention were measured. The results are shown in Table 20. There was no significant difference of the food intake between the control group (provided only 0.5% CMC) and the group treated with the compounds of the present invention.

TABLE 20

| Example Nos. | TC level (mg/dl) | TG level (mg/dl) | NEFA levle ($\mu$Eq/l) |
|---|---|---|---|
| Control | 154 ± 8 | 158 ± 19 | 537 ± 69 |
| Example 5 (10) | 88 ± 6* | 95 ± 17* | 334 ± 55 |
| Example 5 (11) | 91 ± 6* | 90 ± 14* | 227 ± 17* |

*: $p < 0.01$ vs control (5 rats per group)

The hypoglycemic or hypolipidemic effects observed in KKAy mice imply the possibility of preventives and/or remedies for diabetes and hyperlipidemia etc. Cholesterol-lowering and free fatty acid-lowering effects observed in high cholesterol diet-fed rats imply that the compounds of the present invention are useful as preventives and/or remedies of atherosclerosis etc.

The compounds of the present invention possess the hypoglycemic or hypolipidemic (TG, NEFA) effects as well as cholesterol-lowering effect, so they are expected to be more useful to compare with the marketed hypoglycemic or hypolipidemic drugs.

In addition, it has been known that hyperlipidemia, obesity or diabetes are one of cause of uncondition in liver function and hyperlipid in liver. Therefore, the compounds of the present invention are expected to be the drugs to improve liver function which has not been marketed.

Industrial Applicability

The compounds of the formula (I) of the present invention, non-toxic salts thereof, acid addition salts thereof and hydrates thereof have PPAR regulating effect, and therefore are expected to be applied as hypoglycemic agents, hypolipidemic agents, preventives and/or remedies for diseases associated with metabolic disorders (diabetes, obesity, syndrome X, hypercholesterolemia and hyperlipoproteinemia etc.), hyperlipidemia, atherosclerosis, hypertension, circulatory diseases, overeating, coronary heart diseases etc., HDL cholesterol-elevating agents, LDL cholesterol and/or VLDL cholesterol-lowering agents and agents for relieving risk factors of diabetes or syndrome X.

The compounds of formula (I) of the present invention, non-toxic salts thereof, acid addition salts thereof and hydrates thereof have particularly PPARα agonist and/or PPARγ agonist effect, and therefore are thought to be useful as hypoglycemic agents, hypolipidemic agents, preventives and/or remedies for diseases associated with metabolic disorders (diabetes, obesity, syndrome X, hypercholesterolemia, hyperlipoproteinemia etc.), hyperlipidemia, atherosclerosis, hypertension, circulatory diseases and overeating etc. Since they are expected to have HDL cholesterol-elevating effect, LDL cholesterol and/or VLDL cholesterol-lowering effect, inhibition of progress of atherosclerosis and its treatment, and inhibitory effect against obesity, they are also expected to be useful for the treatment and/or prevention of diabetes as hypoglycemic agents, for the amelioration of hypertension, for the relief from risk factors of syndrome X, and as preventives against occurrence of coronary heart diseases.

Toxicity

The toxicity of the compounds of the present invention is very low and therefore, it may be considered that the compounds of the present invention are safe for pharmaceutical use.

Application for Pharmaceuticals

For the purpose above described, the compounds of the present invention of the formula (I), non-toxic salts and acid addition salts thereof and hydrates thereof may be normally administered systemically or locally, usually by oral or parenteral administration.

The doses to be administered are determined depending upon age, body weight, symptom, the desired therapeutic effect, the route of administration, and the duration of the treatment etc. In the human adult, the doses per person per dose are generally between 1 mg and 1000 mg, by oral administration, up to several times per day, and between 0.1 mg and 100 mg, by parenteral administration (preferred into vein) up to several times per day, or continuous administration between 1 and 24 hrs. per day into vein.

As mentioned above, the doses to be used depend upon various conditions. Therefore, there are cases in which doses lower than or greater than the ranges specified above may be used.

The compounds of the present invention may be administered as inner solid compositions or inner liquid compositions for oral administration, or as injections, liniments or suppositories etc. for parenteral administration.

Inner solid compositions for oral administration include compressed tablets, pills, capsules, dispersible powders and granules etc. Capsules contain hard capsules and soft capsules.

In such inner solid compositions, one or more of the active compound(s) is or are, admixed with at least one inert diluent (lactose, mannitol, glucose, microcrystalline cellulose, starch etc.), connecting agents (hydroxypropyl cellulose, polyvinylpyrrolidone, magnesium metasilicate aluminate etc.), disintegrating a, agents (cellulose calcium glycolate etc.), lubricating agents (magnesium stearate etc.), stabilizing agents, assisting agents for dissolving (glutamic acid, asparaginic acid etc.) etc. to prepare pharmaceuticals by known methods. The pharmaceuticals may, if desired, be coated with material such as sugar, gelatin, hydroxypropyl cellulose or hydroxypropyl cellulose phthalate etc., or be coated with two or more films. And further, coating may include containment within capsules of absorbable materials such as gelatin.

Inner liquid compositions for oral administration include pharmaceutically-acceptable water-agents, suspensions, emulsions, syrups and elixirs etc. In such liquid compositions, one or more of the active compound(s) is or are comprised in inert diluent(s) commonly used in the art (purified water, ethanol or mixture thereof etc.). Besides inert diluents, such compositions may also comprise adjuvants such as wetting agents, suspending agents, emulsifying agents, sweetening agents, flavoring agents, perfuming agents, preserving agents and buffer agents etc.

Injections for parenteral administration include solutions, suspensions and emulsions and solid injections which are dissolved or suspended in solvent when it is used. One or more active compound(s) is or are dissolved, suspended or emulsified in a solvent when such compositions are used. Aqueous solutions or suspensions include distilled water for injection and physiological salt solution plant oil, propylene glycol, polyethylene glycol and alcohol such as ethanol etc., and mixture thereof. Such compositions may comprise additional diluents such as stabilizing agent, assisting agents for dissolving (glutamic acid, asparaginic acid, POLYSOLBATE 80 (registered trade mark) etc.), suspending agents, emulsifying agents, dispersing agents, buffer agents, preserving agents etc. They may be sterilized for example, by filtration through a bacteria-retaining filter, by incorporation of sterilizing agents in the compositions or by irradiation. They may also be manufactured in the form of sterile solid compositions and which can be dissolved in sterile water or some other sterile diluent for injection immediately before use.

Other compositions for parenteral administration include liquids for external use, ointments, endermic liniments, aerosols, spray compositions, suppositories and pessaries for vaginal administration etc. which comprise one or more of the active compound(s) and may be prepared by known methods.

Spray compositions may comprise additional substances other than inert diluents: e.g. stabilizing agents such as sodium hydrogen sulfate, stabilizing agents to give isotonicity, isotonic buffer such as sodium chloride, sodium citrate, citric acid. For preparation of such spray compositions, for example, the method described in the U.S. Pat. No. 2,868,691 or 3,095,355 may be used.

BEST MODE FOR CARRYING OUT THE INVENTION

The following Reference Examples and Examples are intended to illustrate, but do not limit the present invention.

The solvents in parenthesis show the developing or eluting solvents and the ratios of the solvents used are by volume in chromatographic separations and TLC.

The solvents in parentheses in NMR show the solvents used for measurements.

REFERENCE EXAMPLE 1 trans-2-Buten-1,4-diol

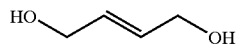

Fumaric acid diethyl ester (1.72 g) was dissolved into benzene (50 ml). Thereto, diisobutylalminium hydride (53 ml, 0.94 M in hexane) was added at 5–10° C. The mixture was stirred at room temperature for 3 hours. To the readction mixture, methanol (6 ml) and water (20 ml) were added. The mixture was stirred at room temperature for 1 hour. The precipitated solid was filtered by Celite. The filtrate was washed by methanol. The methanol solution and filtrate were concentrated to obtain the title compound (0.68 g) having the following physical data.

TLC: Rf 0.15 (ether); NMR (CDCl$_3$): δ 5.68 (t, J=2.5 Hz, 2H), 4.64 (t, J=5.5 Hz, 2H), 3.92 (m, 4H).

REFERENCE EXAMPLE 2 trans-4-(Tetrahydropyran-2-yloxy)-2-buten-1-ol

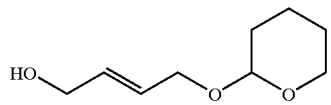

A compound prepared in Reference Example 1 (650 mg) and dihydropyran (0.68 ml) were dissolved into methylene chloride (20 ml). Thereto, pyridinium p-toluenesulfonate (175 mg, abbreviated as PPTS) was added at 0° C. The mixture was stirred at room temperature overnight and added to a cold aqueous saturated solution of sodium chloride. The mixture was extracted with ethyl acetate. The extract was dried over anhydrous magnesium sulfate and concentrated. The residue was purified with silica gel column chromatography (hexane:ethyl acetate=2:1→3:2) to obtain the title compound (346 mg) having the following physical data.

TLC: Rf 0.35 (ethyl acetate:hexane=1:1); NMR (CDCl₃): δ 5.94 (m, 1H), 5.83 (m, 1H), 4.66 (t, J=3.5 Hz, 1H), 4.27 (m, 1H), 4.20–4.15 (m, 2H), 3.99 (m, 1H), 3.88 (m, 1H), 3.52 (m, 1H), 2.00–1.60 (m, 6H).

REFERENCE EXAMPLE 3 trans-1-Methanesulfonyloxy-4-(tetrahydropyran-2-yloxy)-2-butene

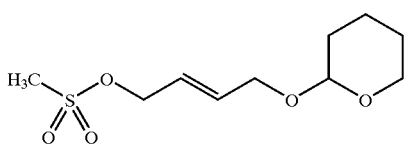

A compound prepared in Reference Example 2 (326 mg) and triethylamine (0.39 ml) were dissolved into methylene chloride (10 ml). Thereto, mesyl chloride (263 mg) was added at 0° C. The mixture was stirred at 0° C. for 1 hour and poured into iced water. The mixture was extracted with ethyl acetate. The extract was washed by an aqueous saturated solution of sodium hydrogencarbonate, water and an aqueous saturated solution of sodium chloride sucessively, dried over anhydrous magnesium sulfate and concentrated to obtain the title compound (438 mg) having the following physical data.

TLC: Rf 0.59 (ethyl acetate:hexane=1:1); NMR (CDCl₃): δ 6.03 (m, 1H), 5.89 (m, 1H), 4.74 (d, J=5.5 Hz, 2H), 4.64 (t, J=3.0 Hz, 1H), 4.29 (m, 1H), 4.02 (m, 1H), 3.87 (m, 1H), 3.52 (m, 1H), 3.02 (s, 3H), 2.00–1.60 (m, 6H).

REFERENCE EXAMPLE 4 trans-1-(2-(5-Methyl-2-phenyloxazol-4-yl) ethoxy)-4-(tetrahydropyran-2-yloxy)-2-butene

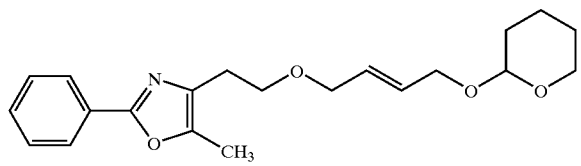

Sodium hydroxide (115 mg, 60% in oil) was washed by hexane three times, and added to tetrahydrofuran (5 ml). Thereto, 2-(5-methyl-2-phenyloxazol-4-yl)ethanol (488 mg) was added at 0° C. The mixture was stirred for 30 minutes. To the reaction mixture, a solution of a compound prepared in Reference Example 3 (410 mg) in tetrahydrofuran (5 ml) was added. The mixture was stirred overnight. To the reaction mixture, iced water was added. The mixture was extracted with ether. The extract was washed by water and an aqueous saturated solution of sodium chloride sucessively, dried over anhydrous magnesium sulfate and concentrated. The residue was purified with silica gel column chromatography (hexane:ethyl acetate=4:1) to obtain the title compound (498 mg) having the following physical data.

TLC: Rf 0.57 (ethyl acetate:hexane=2:3); NMR (CDC₃): δ 7.98 (m, 2H), 7.50–7.35 (m, 3H), 5.95–5.70 (m, 2H), 4.64 (t, J=3.5 Hz, 1H), 4.24 (m, 1H), 4.05–3.80 (m, 4H), 3.71 (t, J=7.0 Hz, 2H), 3.50 (m, 1H), 2.79 (t, J=7.0 Hz, 2H), 2.34 (s, 3H), 2.00–1.45 (m, 6H).

REFERENCE EXAMPLE 5 trans-4-(2-(5-methyl-2-phenyloxazol-4-yl)ethoxy)-2-buten-1-ol

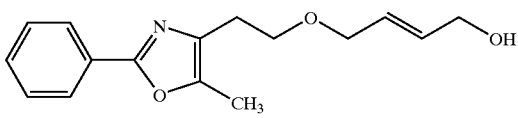

A compound prepared in Reference Example 4 (332 mg) was dissolved into methanol (10 ml). Thereto, p-toluenesulfonic acid monohydrate (19 mg) was added. The mixture was stirred at room temperature for 5 hours and then poured into iced water. The mixture was extracted with ethyl acetate. The extract was washed by water and an aqueous saturated solution of sodium chloride sucessively, dried over anhydrous magnesium sulfate and concentrated to obtain the title compound (255 mg) having the following physical data.

TLC: Rf 0.17 (ethyl acetate:hexane=2:3); NMR (CDCl₃): δ 7.98 (m, 2H), 7.50–7.35 (m, 3H), 5.89 (m, 1H), 5.79 (m, 1H), 4.15 (d, J=4.5 Hz, 2H), 4.01 (d, J=4.5 Hz, 2H), 3.71 (t, J=6.0 Hz, 2H), 2.78 (t, J=6.0 Hz, 2H), 2.34 (s, 3H).

REFERENCE EXAMPLE 6 trans-1-(2-(5-Methyl-2-phenyloxazol-4-yl)ethoxy)-4-(methanesulfonyloxy)-2-butene

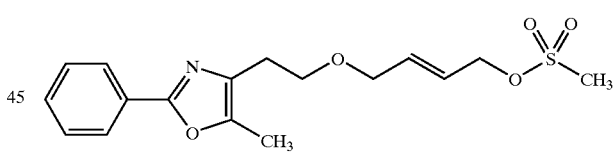

A compound prepared in Reference Example 5 (244 mg) and triethylamine (0.19 ml) were dissolved into methylene chloride (10 ml). Thereto, methanesulfonyl chloride (126 mg) was added at 0° C. The mixture was stirred at 0° C. for 1 hour. The reaction mixture was added to iced water and extracted with ethyl acetate. The extract was washed by an aqueous saturated solution of sodium hydrogencarbonate, water and an aqueous saturated solution of sodium chloride sucessively, dried over anhydrous magnesium sulfate and concentrated to obtain the title compound (315 mg) having the following physical data.

TLC: Rf 0.21 (ethyl acetate:hexane=2:3); NMR (CDCl₃): δ 7.98 (m, 2H), 7.50–7.35 (m, 3H), 5.98 (m, 1H), 5.84 (m, 1H), 4.61 (d, J=5.5 Hz, 2H), 4.04 (dd, J=4.5, 1.0 Hz, 2H), 3.73 (t, J=7.0 Hz, 2H), 2.99 (s, 3H), 2.79 (t, J=7.0 Hz, 2H), 2.35 (s, 3H).

REFERENCE EXAMPLE 7

5-(2-(5-Methyl-2-phenyloxazol-4-yl)ethoxy)pentyl Bromide

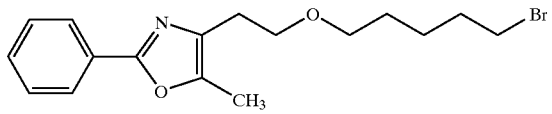

The mixture of 2-(5-methyl-2-phenyloxazol-4-yl)ethanol (2.03 g), 1,5-dibromopentane (4.09 ml), 50% NaOH (4.0 ml) and tributylammonium bromide (0.1 g) was stirred at room temperature overnight. The reaction mixture was diluted with ether, washed by water and an aqueous saturated solution of sodium chloride sucessively, dried over anhydrous magnesium sulfate and concentrated. The residue was purified with silica gel column chromatography (hexane:ethyl acetate=10:1→4:1) to obtain the title compound (3.45 g) having the following physical data.

TLC: Rf 0.36 (ethyl acetate:hexane=1:5); NMR (CDCl$_3$): δ 7.98 (m, 2H), 7.50–7.35 (m, 3H), 3.68 (t, J=7.0 Hz, 2H), 3.46 (t, J=6.0 Hz, 2H), 3.38 (t, J=7.0 Hz, 2H), 2.77 (t, J=7.0 Hz, 2H), 2.34 (s, 3H), 1.82 (m, 2H), 1.70–1.40 (m, 4H).

EXAMPLE 1

2-((2E)-4-(2-(5-Methyl-2-phenyloxazol-4-yl)ethoxy)-2-butenylthio)acetic Acid Methyl Ester

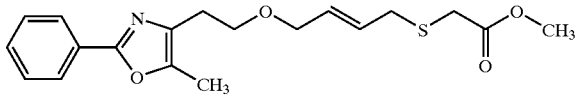

A compound prepared in Reference Example 6 (305 mg), mercaptoacetic acid methyl ester (158 ml) and potassium carbonate (361 mg) were dissolved into acetonitrile (5 ml). Thereto, potassium iodide (17 mg) was added at room temperature. The mixture was stirred overnight. The reaction mixture was added to iced water and then extracted with ether. The extract was washed by 1N—NaOH solution, water and an aqueous saturated solution of sodium chloride sucessively, dried over anhydrous magnesium sulfate and concentrated to obtain the compound (291 mg) of the present invention having the following physical data.

TLC: Rf 0.53 (ethyl acetate:hexane=2:3); NMR (CDCl$_3$): δ 7.98 (m, 2H), 7.50–7.35 (m, 3H), 5.72 (dt, J=15.0, 4.5 Hz, 1H), 5.63 (dt, J=15.0, 6.0 Hz, 1H), 4.00 (d, J=4.5 Hz, 2H), 3.71 (s, 3H), 3.70 (t, J=7.0 Hz, 2H), 3.24 (d, J=6.0 Hz, 2H), 3.16 (s, 2H), 2.78 (t, J=7.0 Hz, 2H), 2.34 (s, 3H).

EXAMPLE 2–EXAMPLE 2(18)

By the same procedures described in Reference Example 4→Reference Example 5→Reference Example 6→Example 1, the following compounds of the present invention were obtained.

In the procedure of Reference Example 4, the following compounds were used as starting materials.

Example 2: cis-1-methanesulfonyloxy-4-(tetrahydropyran-2-yloxy)-2-butene and 2-(5-methyl-2-phenyloxazol-4-yl)ethanol Example 2(1): 1-methanesulfonyloxy-4-(tetrahydropyran-2-yloxy)-2-butyne and 2-(5-methyl-2-phenyloxazol-4-yl)ethanol Example 2(2): trans-4-methanesulfonyloxy-1-(tetrahydropyran-2-yloxy)-2-methyl-2-butene and 2-(5-methyl-2-phenyloxazol-4-yl)ethanol Example 2(3): trans-1-methanesulfonyloxy-4-(tetrahydropyran-2-yloxy)-2-methyl-2-butene and 2-(5-methyl-2-phenyloxazol-4-yl)ethanol Example 2(4): trans-1-methanesulfonyloxy-4-(tetrahydropyran-2-yloxy)-2-butene and 2-(5-methyl-2-(4-methylphenyl)oxazol-4-yl)ethanol Example 2(5): trans-1-methanesulfonyloxy-4-(tetrahydropyran-2-yloxy)-2-butene and 2-(5-methyl-2-(1,3-dioxaindane-5-yl)oxazol-4-yl)ethanol Example 2(6): 1-bromo-4-(tetrahydropyran-2-yloxy)-2-butyne and 2-(5-methyl-2-(4-methylphenyl)oxazol-4-yl)ethanol Example 2(7): 1-bromo-4-(tetrahydropyran-2-yloxy)-2-butyne and 2-(5-methyl-2-(1,3-dioxaindane-5-yl)oxazol-4-yl)ethanol Example 2(8): 1-bromo-4-(tetrahydropyran-2-yloxy)-2-butyne and 2-(5-methyl-2-(4-ethylphenyl)oxazol-4-yl)ethanol Example 2(9): 1-bromo-4-(tetrahydropyran-2-yloxy)-2-butyne and 2-(5-methyl-2-(4-propylphenyl)oxazol-4-yl)ethanol Example 2(10): 1-bromo-4-(tetrahydropyran-2-yloxy)-2-butyne and 2-(5-methyl-2-(4-methylphenyl)oxazol-4-yl)ethanol Example 2(11): 1-bromo-4-(tetrahydropyran-2-yloxy)-2-butyne and 2-(5-methyl-2-(4-methylphenyl)oxazol-4-yl)ethanol Example 2(12): 1-bromo-4-(tetrahydropyran-2-yloxy)-2-butyne and 2-(5-methyl-2-(4-methylphenyl)oxazol-4-yl)ethanol Example 2(13): 1-bromo-4-(tetrahydropyran-2-yloxy)-2-butyne and 2-(5-methyl-2-(4-dimethylaminophenyl)oxazol-4-yl)ethanol Example 2(14): 1-bromo-4-(tetrahydropyran-2-yloxy)-2-butyne and 2-(5-methyl-2-(2-dimethylaminopyridin-5-yl)oxazol-4-yl)ethanol Example 2(15): 1-bromo-4-(tetrahydropyran-2-yloxy)-2-butyne and 2-(5-methyl-2-(4-dimethylaminophenyl)oxazol-4-yl)ethanol Example 2(16): 1-bromo-4-(tetrahydropyran-2-yloxy)-2-butyne and 2-(5-methyl-2-(4-dimethylaminophenyl)oxazol-4-yl)ethanol Example 2(17): 1-bromo-4-(tetrahydropyran-2-yloxy)-2-butyne and 2-(5-methyl-2-(2-dimethylaminopyridin-5-yl)oxazol-4-yl)ethanol Example 2(18): 1-bromo-4-(tetrahydropyran-2-yloxy)-2-butyne and 2-(5-methyl-2-(2-dimethylaminopyridin-5-yl)oxazol-4-yl)ethanol In the procedure of Example 1, the following compounds were used as starting materials.

Example 2–Example 2(9), Example 2(14): mercaptoacetic acid methyl ester

Example 2(13): mercaptoacetic acid ethyl ester

Example 2(10): (2RS)-2-mercaptopropanoic acid ethyl ester

Example 2(11), Example 2(15), Example 2(17): 2-mercapto-2-methylpropanoic acid ethyl ester Example 2(12), Example 2(16), Example 2(18): (1-mercapto)cyclobutane carboxylic acid ethyl ester

EXAMPLE 2

2-((2Z)-4-(2-(5-Methyl-2-phenyloxazol-4-yl)ethoxy)-2-butenylthio)acetic Acid Methyl Ester

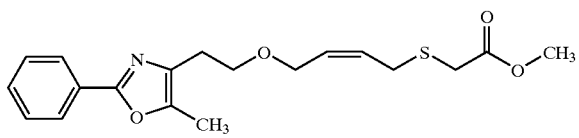

TLC: Rf 0.57 (ethyl acetate:hexane=2:3); NMR (CDCl$_3$): δ 7.98 (m, 2H), 7.50–7.35 (m, 3H), 5.76 (dtt, J=11.0, 6.0, 1.0 Hz, 1H), 5.58 (dtt, J=11.0, 8.0, 1.0 Hz, 1H), 4.07 (dd, J=6.0, 1.0 Hz, 2H), 3.71 (t, J≦7.0 Hz, 2H), 3.71 (s, 3H), 3.31 (dd, J=8.0, 1.0 Hz, 2H), 3.16 (s, 2H), 2.78 (t, J=7.0 Hz, 2H), 2.34 (s, 3H).

EXAMPLE 2(1)

2-(4-(2-(5-Methyl-2-phenyloxazol-4-yl)ethoxy)-2-butynylthio)acetic Acid Methyl Ester

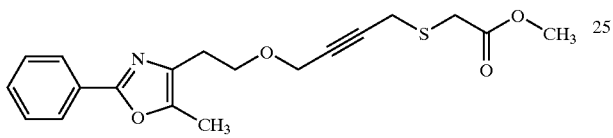

TLC: Rf 0.55 (ethyl acetate:hexane=2:3); NMR (CDCl$_3$): δ 7.98 (m, 2H), 7.50–7.35 (m, 3H), 4.19 (t, J=2.0 Hz, 2H), 3.78 (t, J=7.0 Hz, 2H), 3.73 (s, 3H), 3.44 (t, J=2.0 Hz, 2H), 3.40 (s, 2H), 2.79 (t, J=7.0 Hz, 2H), 2.35 (s, 3H).

EXAMPLE 2(2)

2-((2E)-2-Methyl-4-(2-(5-methyl-2-phenyloxazol-4-yl)ethoxy)-2-butenylthio)acetic Acid Methyl Ester

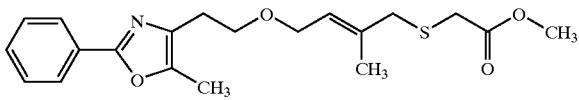

TLC: Rf 0.54 (hexane:ethyl acetate=2:1); NMR (CDCl$_3$): δ 8.01–7.93 (m, 2H), 7.48–7.36 (m, 3H), 5.50 (dt, J=6.5, 1.2 Hz, 1H), 4.05 (d, J=6.5 Hz, 2H), 3.71 (s, 3H), 3.71 (t, J=7.0 Hz, 2H), 3.21 (s, 2H), 3.12 (s, 2H), 2.78 (t, J=7.0 Hz, 2H), 2.34 (s, 3H), 1.74 (d, J=1.2 Hz, 3H).

EXAMPLE 2(3)

2-((2E)-3-Methyl-4-(2-(5-methyl-2-phenyloxazol-4-yl)ethoxy)-2-butenylthio)acetic Acid Methyl Ester

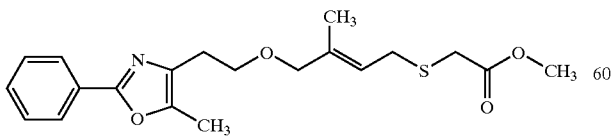

TLC: Rf 0.40 (hexane:ethyl acetate=3:1); NMR (CDC$_3$): δ 8.02–7.92 (m, 2H), 7.48–7.35 (m, 3H), 5.47 (dt, J=8.0, 1.2 Hz, 1H), 3.90 (s, 2H), 3.71 (s, 3H), 3.66 (t, J=7.0 Hz, 2H), 3.30 (d, J=8.0 Hz, 2H), 3.16 (s, 2H), 2.78 (t, J=7.0 Hz, 2H), 2.35 (s, 3H), 1.66 (d, J=1.2 Hz, 3H).

EXAMPLE 2(4)

2-((2E)-4-(2-(5-Methyl-2-(4-methylphenyl)oxazol-4-yl)ethoxy)-2-butenylthio)acetic Acid Methyl Ester

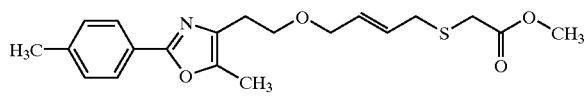

TLC: Rf 0.81 (hexane:ethyl acetate=1:1); NMR (CDCl$_3$): δ 7.86 (d, J=8.0 Hz, 2H), 7.23 (d, J=8.0 Hz, 2H), 5.56–5.78 (m, 2H), 4.00 (d, J=3.8 Hz, 2H), 3.72 (s, 3H), 3.70 (t, J=7.0 Hz, 2H), 3.24 (d, J=5.2 Hz, 2H), 3.16 (s, 2H), 2.77 (t, J=7.0 Hz, 2H), 2.39 (s, 3H), 2.33 (s, 3H).

EXAMPLE 2(5)

2-((2E)-4-(2-(5-Methyl-2-(1,3-dioxaindane-5-yl)oxazol-4-yl)ethoxy)-2-butenylthio)acetic Acid Methyl Ester

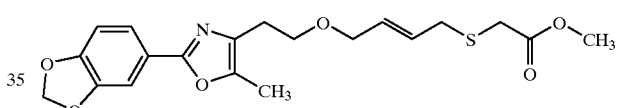

TLC: Rf 0.45 (hexane:ethyl acetate=2:1); NMR (CDCl$_3$): δ 7.51 (dd, J=8.0, 1.7 Hz, 1H), 7.43 (d, J=1.7 Hz, 1H), 6.85 (d, J=8.0 Hz, 1H), 6.01 (s, 2H), 5.57–5.78 (m, 2H), 4.00 (d, J=4.0 Hz, 2H), 3.72 (s, 3H), 3.69 (t, J=6.9 Hz, 2H), 3.24 (d, J=5.6 Hz, 2H), 3.16 (s, 2H), 2.75 (t, J=6.9 Hz, 2H), 2.32 (s, 3H).

EXAMPLE 2(6)

2-(4-(2-(5-Methyl-2-(4-methylphenyl)oxazol-4-yl)ethoxy)-2-butynylthio)acetic Acid Methyl Ester

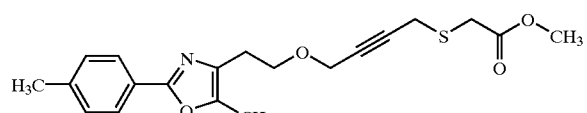

TLC: Rf 0.50 (ethyl acetate:hexane=1:2); NMR (CDCl$_3$): δ 7.85 (d, J=8.0 Hz, 2H), 7.22 (d, J=8.0 Hz, 2H), 4.19 (t, J=2.0 Hz, 2H), 3.78 (t, J=7.0 Hz, 2H), 3.73 (s, 3H), 3.44 (t, J=2.0 Hz, 2H), 3.40 (s, 2H), 2.78 (t, J=7.0 Hz, 2H), 2.38 (s, 3H), 2.33 (s, 3H).

EXAMPLE 2(7)

2-(4-(2-(5-Methyl-2-(1,3-dioxaindane-5-yl)oxazol-4-yl)ethoxy)-2-butynylthio)acetic Acid Methyl Ester

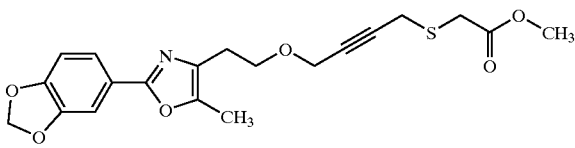

TLC: Rf 0.40 (ethyl acetate:hexane=1:2); NMR (CDCl$_3$): δ 7.81 (dd, J=8.0, 1.5 Hz, 1H), 7.43 (d, J=1.5 Hz, 1H), 6.85 (d, J=8.0 Hz, 1H), 6.01 (s, 2H), 4.20 (t, J=2.0 Hz, 2H), 3.77 (t, J=7.0 Hz, 2H), 3.74 (s, 3H), 3.45 (t, J=2.0 Hz, 2H), 3.41 (s, 2H), 2.77 (t, J=7.0 Hz, 2H), 2.32 (s, 3H).

EXAMPLE 2(8)

2-(4-(2-(5-Methyl-2-(4-ethylphenyl)oxazol-4-yl)ethoxy)-2-butynylthio)acetic Acid Methyl Ester

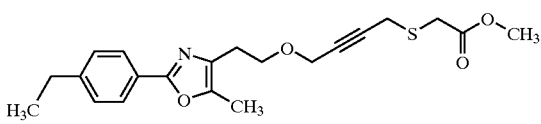

TLC: Rf 0.49 (ethyl acetate:hexane=1:2); NMR (CDCl$_3$): δ 7.88 (d, J=8.2 Hz, 2H), 7.26 (d, J=8.2 Hz, 2H), 4.19 (t, J=2.0 Hz, 2H), 3.78 (t, J=7.0 Hz, 2H), 3.73 (s, 3H), 3.44 (t, J=2.0 Hz, 2H), 3.40 (s, 2H), 2.79 (t, J=7.0 Hz, 2H), 2.68 (q, J=7.6 Hz, 2H), 2.34 (s, 3H), 1.26 (t, J=7.6 Hz, 3H).

EXAMPLE 2(9)

2-(4-(2-(5-Methyl-2-(4-propylphenyl)oxazol-4-yl)ethoxy)-2-butynylthio)acetic Acid Methyl Ester

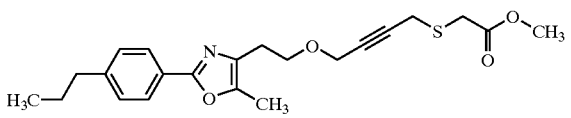

TLC: Rf 0.50 (ethyl acetate:hexane=1:2); NMR (CDC$_3$): δ 7.88 (d, J=8.4 Hz, 2H), 7.23 (d, J=8.4 Hz, 2H), 4.19 (t, J=2.0Hz, 2H), 3.78 (t, J=7.0 Hz, 2H), 3.73 (s, 3H), 3.44 (t, J=2.0 Hz, 2H), 3.40 (s, 2H), 2.79 (t, J=7.0 Hz, 2H), 2.62 (t, J=7.2 Hz, 2H), 2.34 (s, 3H), 1.76–1.56 (m, 2H), 0.94 (t, J=7.4 Hz, 3H).

EXAMPLE 2(10)

(2RS)-2-(4-(2-(5-Methyl-2-(4-methylphenyl)oxazol-4-yl)ethoxy)-2-butynylthio)propanoic Acid Ethyl Ester

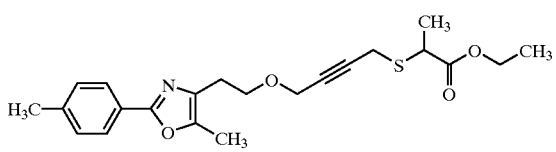

TLC: Rf 0.51 (ethyl acetate:hexane=1:2); NMR (CDCl$_3$): δ 7.86 (d, J=8.4 Hz, 2H), 7.23 (d, J=8.4 Hz, 2H), 4.19 (t, J=2.0 Hz, 2H), 4.18 (q, J=7.2 Hz, 2H), 3.78 (t, J=7.0 Hz, 2H), 3.60 (q, J=7.4 Hz, 1H), (dt, J=16.6, 2.0 Hz, 1H), 3.34 (dt, J=16.6, 2.0 Hz, 1H), 2.78 (t, J=7.0 Hz, 2H), 2.39 (s, 3H), 2.34 (s, 3H), 1.47 (d, J=7.4 Hz, 3H), 1.29 (t, J=7.2 Hz, 3H).

EXAMPLE 2(11)

2-methyl-2-(4-(2-(5-Methyl-2-(4-methylphenyl)oxazol-4-yl)ethoxy)-2-butynylthio)propanoic Acid Ethyl Ester

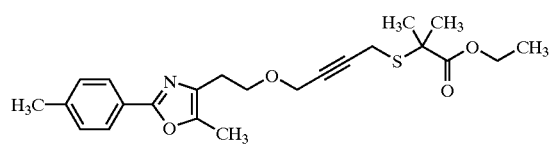

TLC: Rf 0.55 (ethyl acetate hexane=1:2); NMR (CDCl$_3$): δ 7.87 (d, J=8.0 Hz, 2H), 7.22 (d, J=8.0 Hz, 2H), 4.17 (q, J=7.0 Hz, 2H), 4.15 (t, J=2.0 Hz, 2H), 3.77 (t, J=7.0 Hz, 2H), 3.42 (t, J=2.0 Hz, 2H), 2.78 (t, J=7.0 Hz, 2H), 2.39 (s, 3H), 2.34 (s, 3H), 1.53 (s, 6H), 1.28 (t, J=7.0 Hz, 3H).

EXAMPLE 2(12)

1-(4-(2-(5-Methyl-2-(4-methylphenyl)oxazol-4-yl)ethoxy)-2-butynylthio)cyclobutane Carboxylic Acid Ethyl Ester

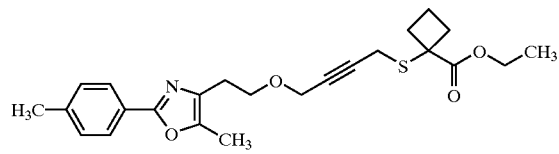

TLC: Rf 0.51 (ethyl acetate:hexane=1:2); NMR (CDCl$_3$): δ 7.87 (d, J=8.0 Hz, 2H), 7.23 (d, J=8.0 Hz, 2H), 4.19 (q, J=7.0 Hz, 2H), 4.15 (t, J=2.0 Hz, 2H), 3.77 (t, J=7.0 Hz, 2H), 3.35 (t, J=2.0 Hz, 2H), 2.78 (t, J=7.0 Hz, 2H), 2.62 (m, 2H), 2.39 (s, 3H), 2.34 (s, 3H), 2.30–2.10 (m, 3H), 1.90 (m, 1H), 1.28 (t, J=7.0 Hz, 3H).

EXAMPLE 2(13)

2-(4-(2-(5-Methyl-2-(4-dimethylaminophenyl)oxazol-4-yl)ethoxy)-2-butynylthio)acetic Acid Ethyl Ester

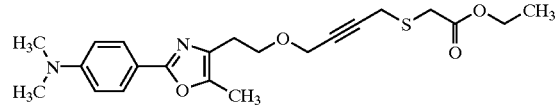

TLC: Rf 0.26 (hexane:ethyl acetate=2:1); NMR (CDCl$_3$): δ 7.83 (d, J=9.0 Hz, 2H), 6.70 (d, J=9.0 Hz, 2H), 4.19 (t, J=2.0 Hz, 2H), 4.18 (q, J=7.2 Hz, 2H), 3.77 (t, J=7.2 Hz, 2H), 3.45 (t, J=2.0 Hz, 2H), 3.38 (s, 2H), 3.01 (s, 6H), 2.77 (t, J=7.2 Hz, 2H), 2.31 (s, 3H), 1.28 (t, J=7.2 Hz, 3H).

EXAMPLE 2(14)

2-(4-(2-(5-Methyl-2-(2-dimethylaminopyridin-5-yl)oxazol-4-yl)ethoxy)-2-butynylthio)acetic Acid Methyl Ester

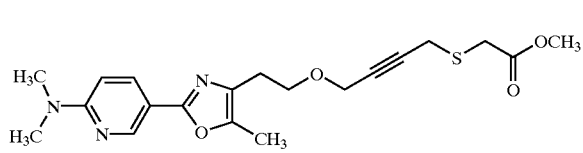

TLC: Rf 0.47 (hexane:ethyl acetate=1:1); NMR (CDCl$_3$): δ 8.73 (m, 1H), 7.99 (dd, J=9.0, 2.5 Hz, 1H), 6.52 (m, 1H), 4.20 (t, J=2.0 Hz, 2H), 3.77 (t, J=7.0 Hz, 2H), 3.74 (s, 3H), 3.44 (t, J=2.0 Hz, 2H), 3.40 (s, 2H), 3.15 (s, 6H), 2.76 (t, J=7.0 Hz, 2H), 2.32 (s, 3H).

EXAMPLE 2(15)

2-Methyl-2-(4-(2-(5-methyl-2-(4-dimethylaminophenyl)oxazol-4-yl)ethoxy)-2-butynylthio)propanoic Acid Ethyl Ester

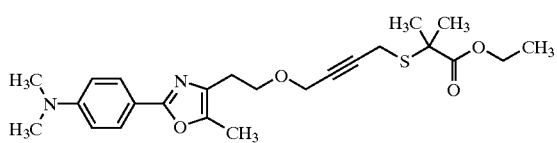

TLC: Rf 0.36 (hexane:ethyl acetate=2:1); NMR (CDCl$_3$): δ 7.83 (d, J=9.0 Hz, 2H), 6.71 (d, J=9.0 Hz, 2H), 4.17 (q, J=7.2 Hz, 2H), 4.16 (t, J=2.0 Hz, 2H), 3.75 (t, J=7.2 Hz, 2H), 3.42 (t, J=2.0 Hz, 2H), 3.01 (s, 6H), 2.76 (t, J=7.2 Hz, 2H), 2.31 (s, 3H), 1.54 (s, 6H), 1.28 (t, J=7.2 Hz, 3H).

EXAMPLE 2(16)

1-(4-(2-(5-Methyl-2-(4-dimethylaminophenyl)oxazol-4-yl)ethoxy)-2-butynylthio)cyclobutane carboxylic Acid Ethyl Ester

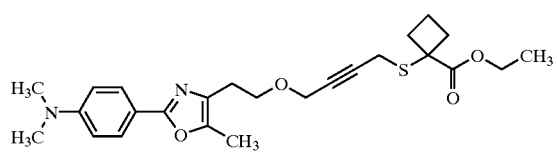

TLC: Rf 0.34 (hexane ethyl acetate=2:1); NMR (CDCl$_3$): δ 7.83 (d, J=9.0 Hz, 2H), 6.70 (d, J=9.0 Hz, 2H), 4.19 (q, J=7.2 Hz, 2H), 4.15 (t, J=2.0 Hz, 2H), 3.76 (t, J=7.0 Hz, 2H), 3.35 (t, J=2.0 Hz, 2H), 3.01 (s, 6H), 2.76 (t, J=7.0 Hz, 2H), 2.71–2.53 (m, 2H), 2.31 (s, 3H), 2.28–2.12 (m, 2H), 1.99–1.68 (m, 2H), 1.29 (t, J=7.2 Hz, 3H).

EXAMPLE 2(17)

2-Methyl-2-(4-(2-(5-methyl-2-(2-dimethylaminopyridin-5-yl)oxazol-4-yl)ethoxy)-2-butynylthio)propanoic Acid Ethyl Ester

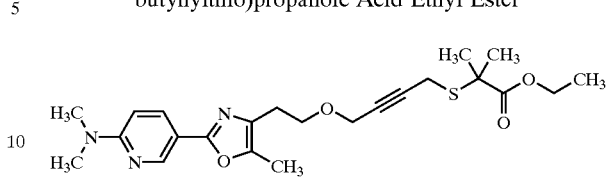

TLC: Rf 0.22 (hexane:ethyl acetate=2:1); NMR (CDCl$_3$): δ 8.73 (dd, J=2.4, 0.6 Hz, 1H), 7.99 (dd, J=9.0, 2.4 Hz, 1H), 6.52 (dd, J=9.0, 0.6 Hz, 1H), 4.19 (q, J=7.2 Hz, 2H), 4.08 (t, J=2.0 Hz, 2H), 4.04 (t, J=2.0 Hz, 2H), 3.58 (t, J=7.2 Hz, 2H), 3.14 (s, 6H), 2.61 (t, J=7.2 Hz, 2H), 2.31 (s, 3H), 1.57 (s, 6H), 1.28 (t, J=7.2 Hz, 3H).

EXAMPLE 2(18)

1-(4-(2-(5-Methyl-2-(2-dimethylaminopyridin-5-yl)oxazol-4-yl)ethoxy)-2-butynylthio)cyclobutane carboxylic Acid Ethyl Ester

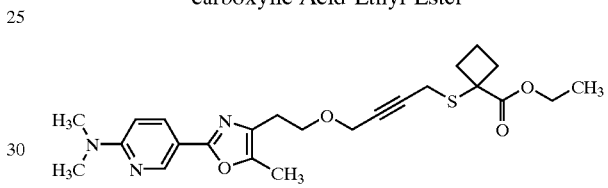

NMR (CDCl$_3$): δ 8.73 (dd, J=2.4, 0.6 Hz, 1H), 7.99 (dd, J=9.0, 2.4 Hz, 1H), 6.52 (dd, J=9.0, 0.6 Hz, 1H), 4.20 (q, J=7.2 Hz, 2H), 4.06 (t, J=2.0 Hz, 2H), 4.03 (t, J=2.0 Hz, 2H), 3.14 (s, 6H), 2.75–2.54 (m, 4H), 2.31 (s, 3H), 2.27–2.08 (m, 3H), 2.00–1.83 (m, 1H), 1.28 (t, J=7.2 Hz, 3H).

EXAMPLE 3

2-(5-(2-(5-Methyl-2-phenyloxazol-4-yl)ethoxy)pentylthio)acetic Acid Methyl Ester

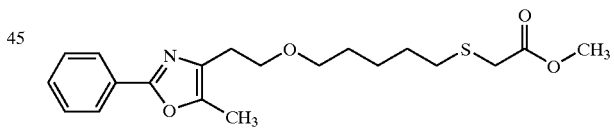

A compound prepared in Reference Example 7 (1.76 g), mercaptoacetic acid methyl ester (0.68 ml) and potassium carbonate (2.07 g) were dissolved into acetonitrile (20 ml). Thereto, potassium iodide (83 mg) was added at room temperature. The mixture was refluxed for 2 hours. The reaction mixture was cooled to room temperature and added to iced water. The mixture was extracted with ether. The extract was washed by 1N—NaOH solution, water and an aqueous saturated solution of sodium chloride sucessively, dried over anhydrous magnesium sulfate and concentrated to obtain the compound (1.72 g) of the present invention having the following physical data.

TLC: Rf 0.20 (ethyl acetate:hexane=1:5); NMR (CDCl$_3$): δ 7.97 (m, 2H), 7.50–7.35 (m, 3H), 3.73 (s, 3H), 3.68 (t, J=7.0 Hz, 2H), 3.44 (t, J=6.0 Hz, 2H), 3.21 (s, 2H), 2.76 (t, J=7.0 Hz, 2H), 2.61 (t, J=7.0 Hz, 2H), 2.34 (s, 3H), 1.75–1.35 (m, 6H).

EXAMPLE 4–EXAMPLE 4(1)

By the same procedures described in Reference Example 7→Example 3, the following compounds of the present invention were obtained.

In the procedure of Reference Example 7, the following compounds were used as starting materials.

Example 4: 1,4-dibromobutane and 2-(5-methyl-2-phenyloxazol-4-yl)ethanol

Example 4(1): 1,3-dibromopropane and 2-(5-methyl-2-phenyloxazol-4-yl)ethanol

EXAMPLE 4

2-(4-(2-(5-Methyl-2-phenyloxazol-4-yl)ethoxy) butylthio)acetic Acid Methyl Ester

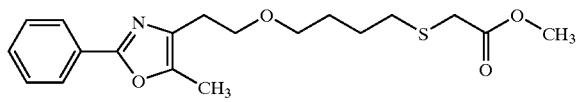

TLC: Rf 0.32 (ethyl acetate:hexane=1:3); NMR (CDCl₃): δ 7.98 (m, 2H), 7.50–7.35 (m, 3H), 3.73 (s, 3H), 3.68 (t, J=7.0 Hz, 2H), 3.46 (m, 2H), 3.20 (s, 2H), 2.76 (t, J=7.0 Hz, 2H), 2.64 (m, 2H), 2.34 (s, 3H), 1.70–1.60 (m, 4H).

EXAMPLE 4(1)

2-(3-(2-(5-Methyl-2-phenyloxazol-4-yl)ethoxy) propylthio)acetic Acid Methyl Ester

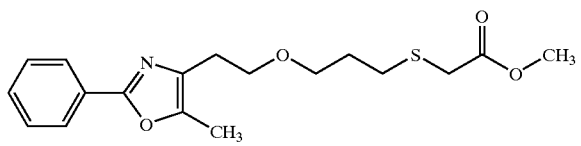

TLC: Rf 0.15 (ethyl acetate:hexane=1:5); NMR (CDCl₃): δ 7.97 (m, 2H), 7.50–7.35 (m, 3H), 3.72 (s, 3H), 3.69 (t, J=6.5 Hz, 2H), 3.53 (t, J=6.0 Hz, 2H), 3.21 (s, 2H), 2.76 (t, J=6.5 Hz, 2H), 2.70 (t, J=6.5 Hz, 2H), 2.34 (s, 3H), 1.85 (m, 2H).

EXAMPLE 5

2-((2E)-4-(2-(5-Methyl-2-phenyloxazol-4-yl) ethoxy)-2-butenylthio)acetic Acid

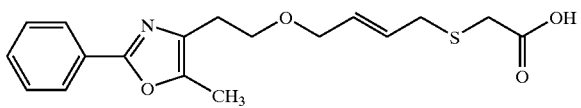

A compound prepared in Example 1 (270 mg) was dissolved into mixture solvent (10 ml, methanol:tetrahydrofuran=1:1). Thereto, 1N NaOH solution (3.75 ml) was added at room temperature. The mixture was stirred for 2 hours and then neutralized by addition of HCl. The mixture was extracted with ethyl acetate. The extract was washed by water and an aqueous saturated solution of sodium chloride sucessively, dried over anhydrous magnesium sulfate and concentrated to obtain the compound (240 mg) of the present invention having the following physical data.

TLC: Rf 0.33 (water:methanol:chloroform=1:10:100); NMR (CDCl₃): δ 7.95 (m, 2H), 7.50–7.40 (m, 3H), 5.82 (dt, J=15.0, 6.5 Hz, 1H), 5.67 (dt, J=15.0, 5.0 Hz, 1H), 4.01 (d, J=5.0 Hz, 2H), 3.66 (t, J=8.0 Hz, 2H), 3.31 (s, 2H), 3.28 (d, J=6.5 Hz, 2H), 2.83 (t, J=8.0 Hz, 2H), 2.35 (s, 3H).

EXAMPLE 5(1)–EXAMPLE 5(17)

By the same procedure described in Example 5 using compounds prepared in Example 2 to Example 2(5), Example 3, Example 4 to Example 4(1), Example 2(6) to Example 2(9) and Example 2(11) to 2(14), the following compounds of the present invention were obtained In case of Example 5(10), Example 5(12) and Example 5(13), recrestallization from mixture solvent of ethyl acetate-hexane was followed after the procedure described in Example 5.

EXAMPLE 5(1)

2-((2Z)-4-(2-(5-Methyl-2-phenyloxazol-4-yl) ethoxy)-2-butenylthio)acetic Acid

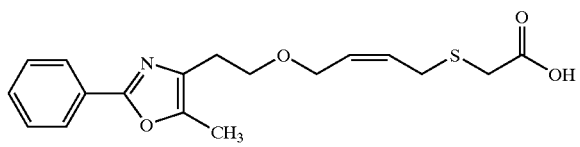

TLC: Rf 0.32 (water:methanol:chloroform=1:10:100); NMR (CDC₃): δ 8.65 (br., 1H), 7.96 (m, 2H), 7.50–7.40 (m, 3H), 5.78 (m, 1H), 5.59 (m, 1H), 4.05 (d, J=6.0 Hz, 2H), 3.67 (t, J=7.0 Hz, 2H), 3.41 (d, J 8.0 Hz, 2H), 3.30 (s, 2H), 2.83 (t, J=7.0 Hz, 2H), 2.34 (s, 3H).

EXAMPLE 5(2)

2-(4-(2-(5-Methyl-2-phenyloxazol-4-yl)ethoxy)-2-butynylthio)acetic Acid

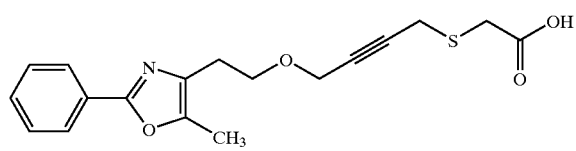

TLC: Rf 0.28 (water:methanol:chloroform=1:10:100); NMR (CDCl₃): δ 7.97 (m, 2H), 7.50–7.40 (m, 3H), 4.23 (t, J=2.0 Hz, 2H), 3.81 (t, J=7.0 Hz, 2H), 3.47 (t, J=2.0 Hz, 2H), 3.46 (s, 2H), 2.87 (t, J=7.0 Hz, 2H), 2.35 (s, 3H).

EXAMPLE 5(3)

2-((2E)-2-Methyl-4-(2-(5-methyl-2-phenyloxazol-4-yl)ethoxy)-2-butenylthio)acetic Acid

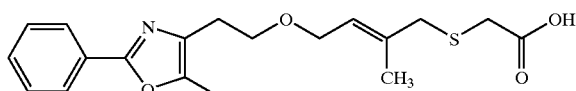

TLC: Rf 0.39 (chloroform:methanol=15:1); NMR (CDCl₃): δ 7.99–7.87 (m, 2H), 7.48–7.38 (m, 3H), 5.52 (dt, J=7.0, 1.5 Hz, 1H), 4.05 (d, J=7.0 Hz, 2H), 3.61 (t, J=8.0 Hz, 2H), 3.30 (s, 2H), 3.22 (s, 2H), 2.79 (t, J=8.0 Hz, 2H), 2.34 (s, 3H), 1.82 (d, J=1.5 Hz, 3H).

EXAMPLE 5(4)

2-((2E)-3-Methyl-4-(2-(5-methyl-2-phenyloxazol-4-yl)ethoxy)-2-butenylthio)acetic Acid

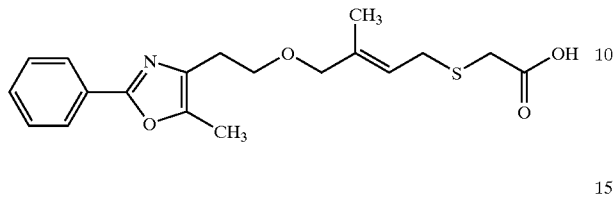

TLC: Rf 0.44 (chloroform:methanol=3:1); NMR (CDCl$_3$): δ 7.98–7.86 (m, 2H), 7.48–7.36 (m, 3H), 5.65 (t, J=8.0 Hz, 1H), 3.92 (s, 2H), 3.63 (t, J=8.0 Hz, 2H), 3.36–3.24 (m, 4H), 2.84 (t, J=8.0 Hz, 2H), 2.35 (s, 3H), 1.69 (s, 3H).

EXAMPLE 5(5)

2-((2E)-4-(2-(5-Methyl-2-(4-methylphenyl)oxazol-4-yl)ethoxy)-2-butenylthio)acetic Acid

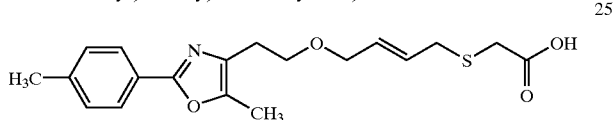

TLC: Rf 0.67 (chloroform:methanol=5:1); NMR (CDCl$_3$): δ 7.82 (d, J=8.2 Hz, 2H), 7.23 (d, J=8.2 Hz, 2H), 5.60–5.90 (m, 2H), 4.00 (d, J=5.4 Hz, 2H), 3.65 (t, J=8.3 Hz, 2H), 3.31 (s, 2H), 3.27 (d, J=6.8 Hz, 2H), 2.81 (t, J=8.3 Hz, 2H), 2.38 (s, 3H), 2.33 (s, 3H).

EXAMPLE 5(6)

2-((2E)-4-(2-(5-Methyl-2-(1,3-dioxaindane-5-yl)oxazol-4-yl)ethoxy)-2-butenylthio)acetic Acid

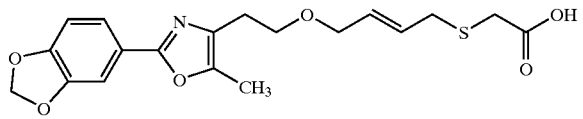

TLC: Rf 0.59 (chloroform:methanol=5:1); NMR (CDCl$_3$): δ 7.49 (dd, J=8.3, 1.7 Hz, 1H), 7.39 (d, J=1.7 Hz, 1H), 6.85 (d, J=8.3 Hz, 1H), 6.02 (s, 2H), 5.59–5.90 (m, 2H), 4.00 (d, J=4.8 Hz, 2H), 3.64 (t, J=8.0 Hz, 2H), 3.31 (s, 2H), 3.27 (d, J=7.0 Hz, 2H), 2.80 (t, J=8.0 Hz, 2H), 2.32 (s, 3H).

EXAMPLE 5(7)

2-(5-(2-(5-Methyl-2-phenyloxazol-4-yl)ethoxy)pentylthio)acetic Acid

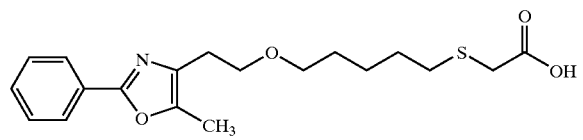

TLC: Rf 0.33 (water:methanol:chloroform=1:10:100); NMR (CDCl$_3$): δ 7.97 (m, 2H), 7.50–7.35 (m, 3H), 3.65 (t, J=7.5 Hz, 2H), 3.49 (t, J=6.0 Hz, 2H), 3.24 (s, 2H), 2.82 (t, J=7.5 Hz, 2H), 2.68 (t, J=7.0 Hz, 2H), 2.34 (s, 3H), 1.80–1.40 (m, 6H).

EXAMPLE 5(8)

2-(4-(2-(5-Methyl-2-phenyloxazol-4-yl)ethoxy)butylthio)acetic Acid

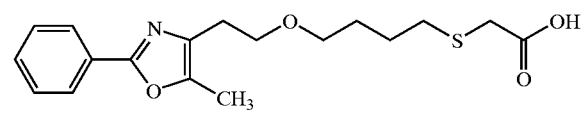

TLC: Rf 0.33 (chloroform:methanol=10:1); NMR (CDCl$_3$): δ 8.00–7.95 (m, 2H), 7.45–7.41 (m, 3H), 3.63 (t, J=7.5 Hz, 2H), 3.55 (m, 2H), 3.27 (s, 2H), 2.84 (t, J=7.5 Hz, 2H), 2.74 (t, J=6.8 Hz, 2H), 2.34 (s, 3H), 1.77–1.71 (m, 4H).

EXAMPLE 5(9)

2-(3-(2-(5-Methyl-2-phenyloxazol-4-yl)ethoxy)propylthio)acetic Acid

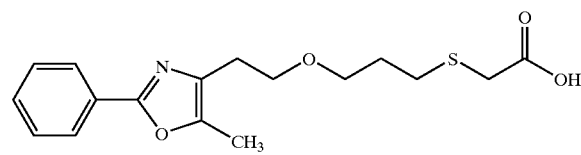

TLC: Rf 0.29 (water:methanol:chloroform=1:10:100) NMR (CDCl$_3$): δ 7.97 (m, 2H), 7.50–7.35 (m, 3H), 3.68 (t, J=7.0 Hz, 2H), 3.61 (t, J=6.5 Hz, 2H), 3.24 (s, 2H), 2.81 (t, J=7.0 Hz, 2H), 2.81 (t, J=7.0 Hz, 2H), 2.34 (s, 3H), 1.86 (m, 2H).

EXAMPLE 5(10)

2-(4-(2-(5-Methyl-2-(4-methylphenyl)oxazol-4-yl)ethoxy)-2-butynylthio)acetic Acid

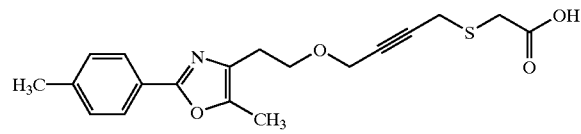

TLC: Rf 0.43 (water:methanol:chloroform=1:10:100); NMR (CDCl$_3$): δ 7.84 (d, J=8.0 Hz, 2H), 7.25 (d, J=8.0 Hz, 2H), 4.23 (t, J=2.0 Hz, 2H), 3.81 (t, J=8.0 Hz, 2H), 3.47 (t, J=2.0 Hz, 2H), 3.46 (s, 2H), 2.86 (t, J=8.0 Hz, 2H), 2.39 (s, 3H), 2.34 (s, 3H).

EXAMPLE 5(11)

2-(4-(2-(5-Methyl-2-(1,3-dioxaindane-5-yl)oxazol-4-yl)ethoxy)-2-butynylthio)acetic Acid

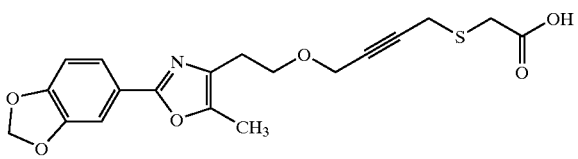

TLC: Rf 0.39 (water:methanol:chloroform=1:10:100); NMR (CDCl₃): δ 7.52 (dd, J=8.0, 1.5 Hz, 1H), 7.42 (d, J=1.5 Hz, 1H), 6.86 (d, J=8.0 Hz, 1H), 6.03 (s, 2H), 4.22 (t, J=2.0 Hz, 2H), 3.80 (t, J=8.0 Hz, 2H), 3.47 (t, J=2.0 Hz, 2H), 3.46 (s, 2H), 2.84 (t, J=8.0 Hz, 2H), 2.32 (s, 3H).

EXAMPLE 5(12)

2-(4-(2-(5-Methyl-2-(4-ethylphenyl)oxazol-4-yl)ethoxy)-2-butynylthio)acetic Acid

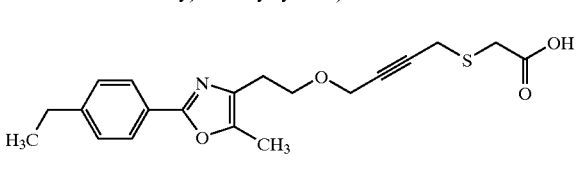

TLC: Rf 0.43 (water:methanol:chloroform=1:10:100); NMR (CDCl₃): δ 7.87 (d, J=8.0 Hz, 2H), 7.27 (d, J=8.0 Hz, 2H), 4.23 (t, J=2.0 Hz, 2H), 3.81 (t, J=8.0 Hz, 2H), 3.47 (t, J=2.0 Hz, 2H), 3.46 (s, 2H), 2.86 (t, J=8.0 Hz, 2H), 2.69 (q, J=7.5 Hz, 2H), 2.34 (s, 3H), 1.26 (t, J=7.5 Hz, 3H).

EXAMPLE 5(13)

2-(4-(2-(5-Methyl-2-(4-propylphenyl)oxazol-4-yl)ethoxy)-2-butynylthio)acetic Acid

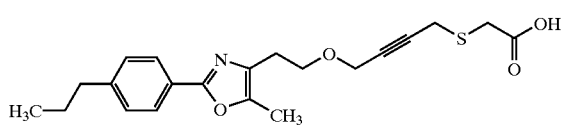

TLC: Rf 0.43 (water:methanol:chloroform=1:10:100); NMR (CDC₃): δ 7.87 (d, J=8.0 Hz, 2H), 7.25 (d, J=8.0 Hz, 2H), 4.23 (t, J=2.0 Hz, 2H), 3.81 (t, J=8.0 Hz, 2H), 3.48 (t, J=2.0 Hz, 2H), 3.47 (s, 2H), 2.86 (t, J=8.0 Hz, 2H), 2.62 (t, J=7.5 Hz, 2H), 2.34 (s, 3H), 1.66 (m, 2H), 0.94 (t, J=7.5 Hz, 3H).

EXAMPLE 5(14)

2-Methyl-2-(4-(2-(5-methyl-2-(4-methylphenyl)oxazol-4-yl)ethoxy)-2-butynylthio)propanoic Acid

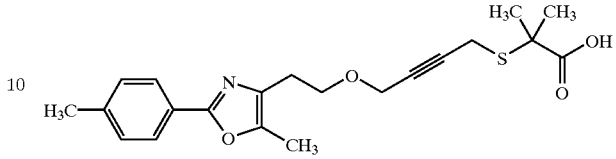

TLC: Rf 0.30 (methanol:chloroform=1:50); NMR (CDCl₃): δ 7.84 (d, J=8.5 Hz, 2H), 7.22 (d, J=8.5 Hz, 2H), 4.21 (t, J=2.0 Hz, 2H), 3.88 (t, J=7.0 Hz, 2H), 3.45 (t, J=2.0 Hz, 2H), 2.89 (t, J=7.0 Hz, 2H), 2.39 (s, 3H), 2.33 (s, 3H), 1.60 (s, 6H).

EXAMPLE 5(15)

1-(4-(2-(5-Methyl-2-(4-methylphenyl)oxazol-4-yl)ethoxy)-2-butynylthio)cyclobutane Carboxylic Acid

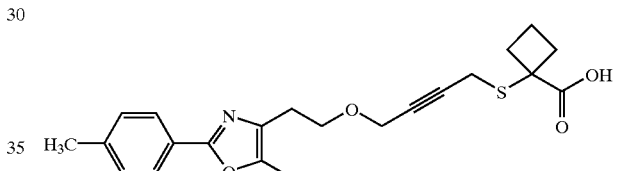

TLC: Rf 0.26 (methanol:chloroform=1:50); NMR (CDCl₃): δ 7.85 (d, J=8.5 Hz, 2H), 7.24 (d, J=8.5 Hz, 2H), 4.20 (t, J=2.0 Hz, 2H), 3.88 (t, J=8.5 Hz, 2H), 3.38 (t, J=2.0 Hz, 2H), 2.89 (t, J=8.5 Hz, 2H), 2.74 (m, 2H), 2.39 (s, 3H), 2.36 (s, 3H), 2.30–1.80 (m, 4H).

EXAMPLE 5(16)

2-(4-(2-(5-Methyl-2-(4-dimethylaminophenyl)oxazol-4-yl)ethoxy)-2-butynylthio)acetic Acid

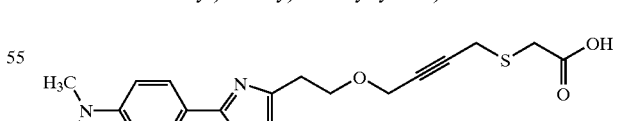

TLC: Rf 0.58 (chloroform:methanol=4:1); NMR (CDCl₃): δ 7.82 (d, J=9.0 Hz, 2H), 6.70 (d, J=9.0 Hz, 2H), 4.22 (t, J=2.0 Hz, 2H), 3.80 (t, J=8.4 Hz, 2H), 3.47 (t, J=2.0 Hz, 2H), 3.46 (s, 2H), 3.03 (s, 6H), 2.84 (t, J=8.4 Hz, 2H), 2.31 (s, 3H).

EXAMPLE 5(17)

2-(4-(2-(5-Methyl-2-(2-dimethylaminopyridin-5-yl)oxazol-4-yl)ethoxy)-2-butynylthio)acetic Acid

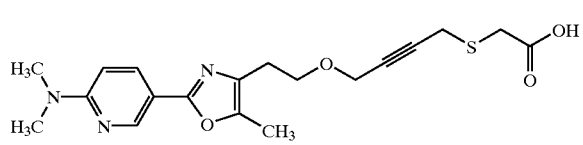

TLC: Rf 0.43 (chloroform:methanol=10:1); NMR (CDCl3): δ 8.73 (d, J=2.5 Hz, 1H), 7.99 (dd, J=9.0, 2.5 Hz, 1H), 6.54 (d, J=9.0 Hz, 1H), 4.22 (t, J=2.0 Hz, 2H), 3.80 (t, J=8.2 Hz, 2H), 3.47 (t, J=2.0 Hz, 2H), 3.46 (s, 2H), 3.15 (s, 6H), 2.84 (t, J=8.2 Hz, 2H), 2.32 (s, 3H).

EXAMPLE 6

2-((2E)-4-(2-(5-Methyl-2-phenyloxazol-4-yl)ethoxy)-2-butenylthio)acetic Acid Sodium Salt

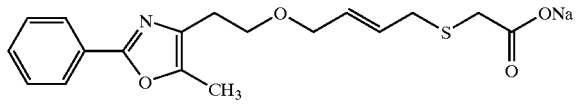

A compound prepared in Example 5 (208 mg) was dissolved into dioxane (5 ml). Thereto, 1N—NaOH (0.60 ml) was added at room temperature. The mixture was stirred for 1 hour. The reaction mixture was freezed-dry to obtain the compound (192 mg) of the present invention having the following physical data.

TLC: Rf 0.33 (water:methanol:chloroform=1:10:100); NMR (DMSO-d6): δ 7.90 (m, 2H), 7.55–7.40 (m, 3H), 5.63 (dt, J=15.0, 6.0 Hz, 1H), 5.51 (dt, J=15.0, 4.5 Hz, 1H), 3.91 (d, J=4.5 Hz, 2H), 3.59 (t, J=7.0 Hz, 2H), 3.09 (d, J=6.0 Hz, 2H), 2.83 (s, 2H), 2.69 (t, J=7.0 Hz, 2H), 2.32 (s, 3H).

EXAMPLE 6(1)–EXAMPLE 6(8)

By the same procedure described in Example 6 using compounds prepared in Example 5(1) to Example 5(2) and Example 5(4) to Example 5(9), the following compounds of the present invention were obtained

EXAMPLE 6(1)

2-((2Z)-4-(2-(5-Methyl-2-phenyloxazol-4-yl)ethoxy)-2-butenylthio)acetic Acid Sodium Salt

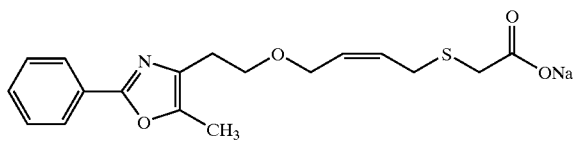

TLC: Rf 0.33 (water:methanol:chloroform=1:10:100); NMR (DMSO-d6): δ 7.90 (m, 2H), 7.55–7.40 (m, 3H), 5.65–5.40 (m, 2H), 4.05 (m, 2H), 3.61 (t, J=7.0 Hz, 2H), 3.18 (m, 2H), 2.86 (s, 2H), 2.70 (t, J=7.0 Hz, 2H), 2.34 (s, 3H).

EXAMPLE 6(2)

2-(4-(2-(5-Methyl-2-phenyloxazol-4-yl)ethoxy)-2-butynylthio)acetic Acid Sodium Salt

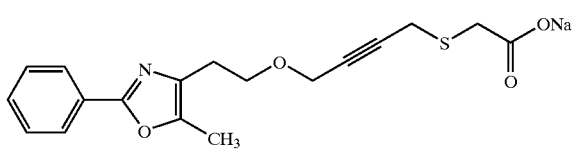

TLC: Rf 0.43 (chloroform:methanol=9:1); NMR (DMSO-d6): δ 7.87–7.92 (m, 2H), 7.46–7.51 (m, 3H), 4.16 (t, J=2.0 Hz, 2H), 3.66 (t, J=6.8 Hz, 2H), 3.38 (t, J=2.0 Hz, 2H), 3.05 (s, 2H), 2.71 (t, J=6.8 Hz, 2H), 2.32 (s, 3H).

EXAMPLE 6(3)

2-((2E)-3-Methyl-4-(2-(5-methyl-2-phenyloxazol-4-yl)ethoxy)-2-butenylthio)acetic Acid Sodium Salt

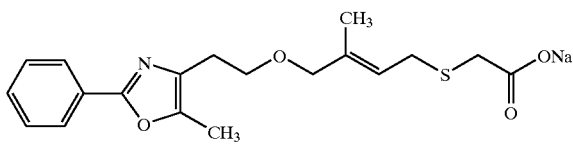

TLC: Rf 0.44 (chloroform:methanol 15:1); NMR (CDCl3): δ 7.98–7.84 (m, 2H), 7.42–7.29 (m, 3H), 5.44 (t, J=7.5 Hz, 1H), 3.79 (s, 2H), 3.57 (t, J=7.0 Hz, 2H), 3.18 (s, 2H), 3.13 (d, J=7.5 Hz, 2H), 2.71 (t, J=7.0 Hz, 2H), 2.26 (s, 3H), 1.57 (s, 3H).

EXAMPLE 6(4)

2-((2E)-4-(2-(5-Methyl-2-(4-methylphenyl)oxazol-4-yl)ethoxy)-2-butenylthio)acetic Acid Sodium Salt

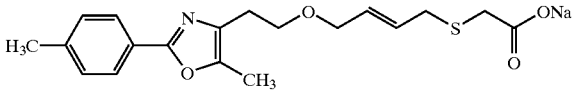

TLC Rf 0.62 (chloroform:methanol=5:1); NMR (DMSO-d6): δ 7.78 (d, J=8.0 Hz, 2H), 7.29 (d, J=8.0 Hz, 2H), 5.46–5.70 (m, 2H), 3.91 (d, J=4.2 Hz, 2H), 3.58 (t, J=7.0 Hz, 2H), 3.10 (d, J=5.4 Hz, 2H), 2.86 (s, 2H), 2.68 (t, J=7.0 Hz, 2H), 2.34 (s, 3H), 2.31 (s, 3H).

EXAMPLE 6(5)

2-((2E)-4-(2-(5-Methyl-2-(1,3-dioxaindane-5-yl)oxazol-4-yl)ethoxy)-2-butenylthio)acetic Acid Sodium Salt

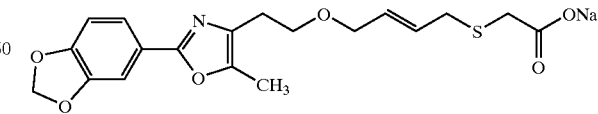

TLC: Rf 0.56 (chloroform:methanol=5:1); NMR (DMSO-d6): δ 7.42 (dd, J=8.2, 1.7 Hz, 1H), 7.34 (d, J=1.7 Hz, 1H), 7.01 (d, J=8.2 Hz, 1H), 6.09 (s, 2H), 5.46–5.70 (m, 2H), 3.91 (d, J=2.8 Hz, 2H), 3.57 (t, J=7.0 Hz, 2H), 3.10 (d, J=5.6 Hz, 2H), 2.86 (s, 2H, 2.66 (t, J=7.0 Hz, 2H), 2.29 (s, 3H).

EXAMPLE 6(6)

2-(5-(2-(5-Methyl-2-phenyloxazol-4-yl)ethoxy)pentylthio)acetic Acid Sodium Salt

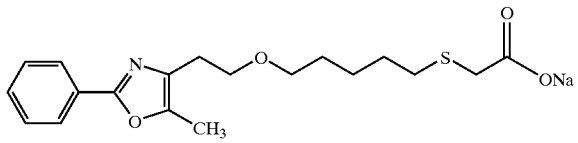

TLC: Rf 0.33 (water:methanol:chloroform=1:10:100); NMR (DMSO-$d_6$): δ 7.90 (m, 2H), 7.55–7.40 (m, 3H), 3.59 (t, J=7.0 Hz, 2H), 3.38 (t, J=6.0 Hz, 2H), 2.89 (s, 2H), 2.69 (t, J=7.0 Hz, 2H), 2.45 (t, J=7.5 Hz, 2H), 2.33 (s, 3H), 1.60–1.20 (m, 6H).

EXAMPLE 6(7)

2-(4-(2-(5-Methyl-2-phenyloxazol-4-yl)ethoxy)butylthio)acetic Acid Sodium Salt

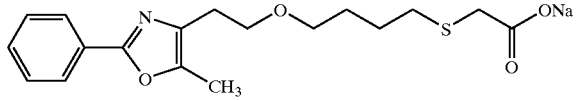

TLC: Rf 0.33 (water:methanol:chloroform=1:10:100); NMR (DMSO-$d_6$): δ 7.90 (m, 2H), 7.55–7.40 (m, 3H), 3.59 (t, J=7.0 Hz, 2H), 3.39 (t, J=6.0 Hz, 2H), 2.88 (s, 2H), 2.69 (t, J=7.0 Hz, 2H), 2.46 (t, J=6.5 Hz, 2H), 2.33 (s, 3H), 1.65–1.40 (m, 4H).

EXAMPLE 6(8)

2-(3-(2-(5-Methyl-2-phenyloxazol-4-yl)ethoxy)propylthio)acetic Acid Sodium Salt

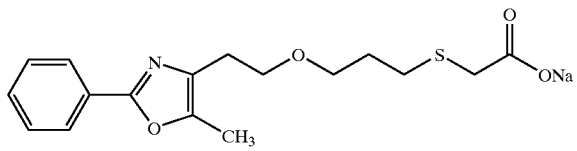

TLC: Rf 0.29 (water:methanol:chloroform=1:10:100); NMR (DMSO-$d_6$): δ 7.90 (m, 2H), 7.55–7.40 (m, 3H), 3.59 (t, J=7.0 Hz, 2H), 3.45 (t, J=6.5 Hz, 2H), 2.91 (s, 2H), 2.69 (t, J=7.0 Hz, 2H), 2.50 (t, J=7.0 Hz, 2H), 2.33 (s, 3H), 1.70 (m, 2H).

EXAMPLE 7

(2RS)-2-(4-(2-(5-Methyl-2-(4-propylphenyl)oxazol-4-yl)ethoxy)-2-butynylthio)propanoic Acid Sodium Salt

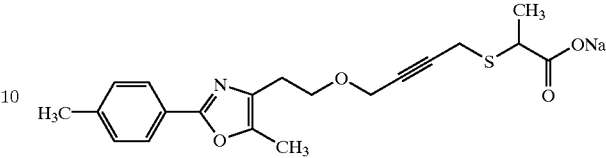

By the same procedures described in Example 5→Example 6 using a compound prepared in Example 2(10), the compound of the present invention having the following physical data was obtained.

TLC: Rf 0.55 (ethyl acetate); NMR (CD$_3$OD): δ 7.83 (d, J=8.4 Hz, 2H), 7.28 (d, J=8.4 Hz, 2H), 4.17 (t, J=2.0 Hz, 2H), 3.75 (t, J=6.6 Hz, 2H), 3.51 (q, J=7.0 Hz, 1H), 3.41–3.35 (t, J=2.0 Hz, 2H), 2.76 (t, J=6.6 Hz, 2H), 2.38 (s, 3H), 2.35 (s, 3H), 1.41 (d, J=7.0Hz, 3H).

EXAMPLE 8

2-(4-(2-(5-Methyl-2-(4-methylphenyl)oxazol-4-yl)ethoxy)-2-butylsulfinyl)acetic Acid

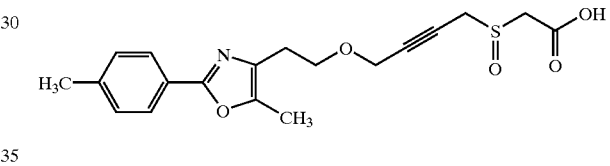

To a solution of a compound prepared in Example 5(10) (1.002 g) in THF (200 ml), a solution of OXONE (trade name) (1.029 g) in water (100 ml) was added at 0° C. The mixture was stirred at 0° C. for 20 minutes. The reaction mixture was poured into iced water and extracted with ethyl acetate. The extract was washed by water and an aqueous saturated solution of sodium chloride, sucessively, dried over anhydrous magnesium sulfate and concentrated. The residue was purified with silica gel column chromatography (chloroform:methanol=50:1→20:1→chloroform:methanol:water=4:1:0.1) to obtain the title compound (0.5994 g) having the following physical data.

TLC: Rf 0.20 (chloroform:methanol:acetic acid=9:1:0.3); NMR (CDCl3): δ 7.82 (d, J=7.8 Hz, 2H), 7.21 (d, J=7.8 Hz, 2H), 4.18 (m, 2H), 3.64–3.98 (m, 6H), 2.76 (t, J=6.9 Hz, 2H), 2.36 (s, 3H), 2.30 (s, 3H).

EXAMPLE 9

2-(4-(2-(5-Methyl-2-(4-methylphenyl)oxazol-4-yl)ethoxy)-2-butynylsulfonyl)acetic Acid

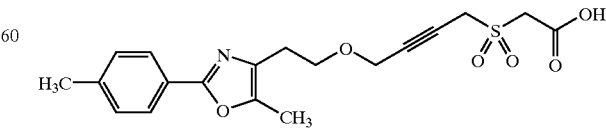

To a solution of a compound prepared in Example 5(10) (1.000 g) in THF (20 ml), a solution of OXONE (trade name) (3.421 g) in water (10 ml) was added at 0° C. The mixture was stirred at room temperature for 4 hours. The reaction mixture was poured into iced water and extracted with ethyl acetate. The extract was washed by water and an aqueous saturated solution of sodium chloride, sucessively, dried over anhydrous magnesium sulfate and concentrated. The residue was purified with silica gel column chromatography (chloroform:methanol=20:1) to obtain the title compound (0.678 g) having the following physical data.

TLC: Rf 0.58 (chloroform:methanol:acetic acid= 50:20:1); NMR (CDCl3): δ 7.86 (d, J=8.0 Hz, 2H), 7.28 (d, J=8.0 Hz, 2H), 4.22–4.26 (m, 6H), 3.76 (t, J=8.1 Hz, 2H), 2.85 (t, J=8.1 Hz, 2H), 2.41 (s, 3H), 2.35 (s, 3H).

REFERENCE EXAMPLE 8

5-Hexynoic Acid (3-Methyloxetan-3-yl)methyl Ester

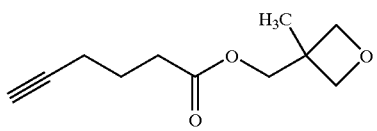

To a solution of 5-hexynoic acid (10.0 g) and 3-methyl-3-oxetane methanol (10.0 g) in methylene chloride (50 ml), 1-ethyl-3-(3-dimethylaminopropyl)carbodiimide hydrochloride (20.5 g), and 4-dimethylaminopyridine (1.09 g) were added under cooling with ice. The mixture was stirred at room temperature for 45 minutes. The reaction mixture was poured into iced water and extracted with ethyl acetate. The organic layer was washed by water and an aqueous saturated solution of sodium chloride, sucessively, dried over anhydrous magnesium sulfate and concentrated. The residue was purified with silica gel column chromatography (n-hexane:ethyl acetate=4:1) to obtain the title compound (16.7 g) having the following physical data.

TLC: Rf 0.38 (n-hexane:ethyl acetate=3:1); NMR (CDCl₃): δ 4.52 (d, J=6.0 Hz, 2H), 4.42 (d, J=6.0 Hz, 2H), 4.18 (s, 2H), 2.52 (t, J=7.0 Hz, 2H), 2.29 (dt, J=2.6, 7.0 Hz, 2H), 1.98 (dt, J=2.6 Hz, 1H), 1.87 (tt, J=7.0, 7.0 Hz, 2H), 1.34 (s, 3H).

REFERENCE EXAMPLE 9

1-(4-Methyl-2,6,7-trioxabicyclo[2.2.2]octan-1-yl)-4-hexyne

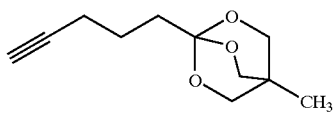

To a solution of a compound prepared in Reference Example 8 (16.7 g) in methylene chloride (200 ml), trifluoro borodiethylether complex (2.6 ml) was added at −20° C. The mixture was stirred at 0° C. overnight. To the reaction mixture, triethylamine (11.85 ml) was added. The mixture was filtered by Celite (trade mark). The filtrate was concentrated. The residue was purified with silica gel column chromatography (1% triethylamine-methylene chloride) to obtain the title compound (14.7 g) having the following physical data.

TLC: Rf 0.58 (n-hexane:ethyl acetate=3:1); NMR (CDCl₃): δ 3.89 (s, 6H), 2.22 (dt, J=2.7, 6.6 Hz, 2H), 1.93 (dt, J=2.7 Hz, 1H), 1.60–1.84 (m, 4H), 0.80 (s, 3H).

REFERENCE EXAMPLE 10

6-(4-Methyl-2,6,7-trioxabicyclo[2.2.2]octan-1-yl)-2-hexyne-1-ol

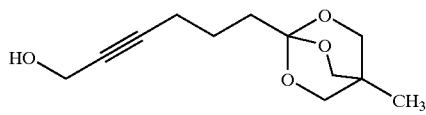

To a solution of a compound prepared in Reference Example 9 (7.58 g) in THF (70 ml), a solution of 1.6 M n-butyllithium hexane (26.6 ml) was added at −78° C. The mixture was stirred for at−780C for 10 minutes. Thereto, p-formaldehyde (1.93 g) was added. The mixture was stirred at room temperature for 5 hours. The reaction mixture was poured into iced water and extracted with ethyl acetate. The organic layer was washed by an aqueous saturated solution of sodium chloride, dried over anhydrous magnesium sulfate and concentrated. The residue was purified with silica gel column chromatography (n-hexane:ethyl to acetate=2:1, containing 1% triethylamine) to obtain the title compound (6.21 g) having the following physical data.

TLC: Rf 0.41 (n-hexane:ethyl acetate=1:1); NMR (CDCl₃): δ 4.22 (t, J=2.2 Hz, 2H), 3.89 (s, 6H), 2.25 (dt, J=7.0, 2.2 Hz, 2), 1.55–1.83 (m, 4H), 0.80 (s, 3H).

REFERENCE EXAMPLE 11

1-Iodo-6-(4-methyl-2,6,7-trioxabicyclo[2.2.2]octan-1-yl)-2-hexyne

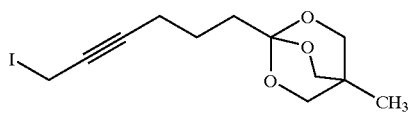

To a solution of a compound prepared in Reference Example 10 (6.21 g) in benzene (130 ml), triphenylphosphine (9.36 ml) and imidazole (2.17 g) were added. To the mixture, iodide (8.36 g) was added under cooling with ice. The mixture was stirred at room temperature for 4.5 hours. The reaction mixture was filtered by Celite (trade mark) and filtrate was concentrated. The residue was purified with silica gel column chromatography (n-hexane:ethyl acetate= 25:1→5:1, containing 1% triethylamine) to obtain the title compound (1.90 g) having the following physical data.

TLC: Rf 0.62 (n-hexane:ethyl acetate=2:1); NMR (CDCl₃): δ 3.89 (s, 6H), 3.69 (t, J=2.4 Hz, 2H), 2.23 (tt, J=6.8, 2.4 Hz, 2H), 1.57–1.80 (m, 4H), 0.80 (s, 3H).

REFERENCE EXAMPLE 12

1-(2-(5-Methyl-2-(1,3-dioxaindane-5-yl)oxazol-4-yl) ethoxy)-6-(4-methyl-2,6,7-trioxabicyclo[2.2.2]octan-1-yl)-2-hexyne

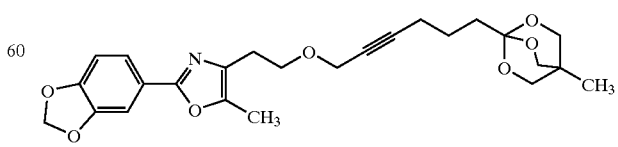

2-(5-methyl-2-(1,3-dioxaindane-5-yl)oxazol-4-yl)ethanol (0.65 g) was dissolved into mixture solvent of THF/DMF (1:1) (14 ml). Thereto, sodium hydroxide (0.116 g) was added under cooling with ice. The mixture was stirred at room temperature for 2 hours. To the reaction mixture, a solution of a compound prepared in Reference Example 11 (0.93 g) in THF (7 ml) was added. The mixture was stirred at room temperature for 6 hours and then at 50° C. overnight. The reaction mixture was poured into iced water (containing 3 ml of triethylamine) and extracted with ethyl acetate. The organic layer was washed by water and an aqueous saturated solution of sodium chloride, sucessively, dried over anhydrous magnesium sulfate and concentrated. The residue was purified with silica gel column chromatography (n-hexane:ethyl acetate=2:1) to obtain the title compound (0.393 g) having the following physical data.

TLC: Rf 0.39 (n-hexane:ethyl acetate=1:1); NMR (CDCl$_3$): δ 7.52 (dd, J=8.4,1.6 Hz, 1H), 7.44 (d, J=1.6 Hz, 1H), 6.85 (d, J=8.4 Hz, 1H), 6.01 (s, 2H), 4.12 (t, J=2.2 Hz, 2H), 3.88 (s, 6H), 3.74 (t, J=7.0 Hz, 2H), 2.76 (t, J=7.0 Hz, 2H), 2.32 (s, 3H), 2.24 (tt, J=6.8, 2.2 Hz, 2H), 1.60–1.83 (m, 4H), 0.79 (s, 3H).

EXAMPLE 10

7-(2-(5-Methyl-2-(1,3-dioxaindane-5-yl)oxazol-4-yl)ethoxy)-5-heptynoic Acid

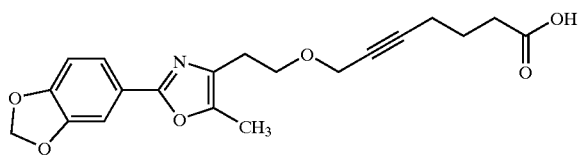

A compound prepared in Reference Example 12 (0.393 g) was dissolved into 1,4-dioxane (5 ml). Thereto, 1M HCl (2.2 ml) was added under cooling with ice. The mixture was stirred at room temperature for 30 minutes and then cooled with ice again. Thereto, a solution of 2 M sodium hydroxide (3.2 ml) was added. The mixture was stirred at room temperature for 1 hour. The reaction mixture was poured into iced water. The back-extraction of the mixture with diethyl ether was carried out. Water layer was acidified by hydrochloric acid and extracted with ethyl acetate. The organic layer was washed by water and an aqueous saturated solution of sodium chloride, sucessively, dried over anhydrous magnesium sulfate and concentrated. The residue was purified with silica gel column chromatography (chloroform:methanol=100:1) to obtain the title compound (0.276 g) having the following physical data.

TLC: Rf 0.39 (chloroform:methanol=15:1); NMR (CDCl$_3$): δ 7.51 (dd, J=8.0, 1.6 Hz, 1H), 7.42 (d, J=1.6 Hz, 1H), 6.86 (d, J=8.0 Hz, 1H), 6.02 (s, 2H), 4.16 (t, J=2.1 Hz, 2H), 3.78 (t, J=7.6 Hz, 2H), 2.81 (t, J=7.6 Hz, 2H), 2.49 (t, J=6.5 Hz, 2H), 2.37 (m, 2H), 2.32 (s, 3H), 1.90 (tt, J=6.5, 6.2 Hz, 2H).

EXAMPLE 11

7-(2-(5-Methyl-2-(4-methylphenyl)oxazol-4-yl)ethoxy)-5-heptynoic Acid

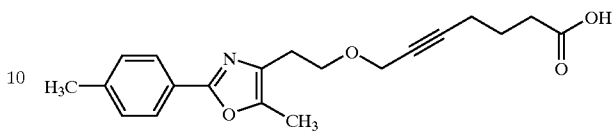

By the same procedures described in Reference Example 12→Example 10 using 2-(5-methyl-2-(4-methylphenyl)oxazol-4-yl)ethanol, the title compound having the following physical data was obtained.

TLC: Rf 0.38 (chloroform:methanol=15:1); NMR (CDCl3): δ 7.85 (d, J=8.2 Hz, 2H), 7.24 (d, J=8.2 Hz, 2H), 4.16 (t, J=2.1 Hz, 2H), 3.79 (t, J=7.8 Hz, 2H), 2.83 (t, J=7.8 Hz, 2H), 2.49 (t, J=6.5 Hz, 3H), 2.37 (m, 2H), 2.34 (s, 3H), 1.89 (tt, J=6.5, 6.5 Hz, 2H).

FORMULATION EXAMPLE

FORMULATION EXAMPLE 1

The following compounds were admixed in conventional method and punched out to obtain 100 tablets each containing 100 mg of active ingredient.

| | |
|---|---|
| 2-((2E)-4-(2-(5-methyl-2-phenyloxazol-4-yl)ethoxy)-2-butenylthio)acetic acid | 10.0 g |
| Cellulose calcium glycolate (disintegrating agent) | 0.2 g |
| Magnesium stearate (lubricating agent) | 0.1 g |
| Micro crystalline cellulose | 9.7 g |

FORMULATION EXAMPLE 2

The following components were admixed in a conventional method, and the solution was sterilized in a conventional method, placed 5 ml portions into ampoules and freeze-dried in a conventional method to obtain 100 ampoules each containing 20 mg of active ingredient.

| | |
|---|---|
| 2-((2E)-4-(2-(5-methyl-2-phenyloxazol-4-yl)ethoxy)-2-butenylthio)acetic acid | 2.0 g |
| Mannit | 5.0 g |
| Distilled water | 500 ml |

What is claimed is:

1. A compound of the formula (I)

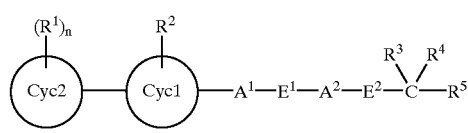

(wherein, $A^1$ is C1–4 alkylene, $A^2$ is C2–8 alkylene, C3–8 alkenylene or C3–8 alkynylene, $E^1$ is —O— or —S—, $E^2$ is —CH$_2$—, —O—, or —S(O)$_m$—.

m is 0, 1 or 2, each $R^1$ in $(R^1)_n$ independently, is hydrogen, C1–8 alkyl, halogen, C1–4 alkoxy, C1–4 alkylthio, nitro, NR$^7$R$^8$ (in which R$^7$ and R$^8$ each independently, is C1–4 alkyl), cyano, trifluoromethyl, trifluoromethyloxy, carbocyclic ring or heterocyclic ring (in which carbocyclic ring and heterocyclic ring may be substituted with the group selected from C1–4 alkyl, C1–4 alkoxy, halogen or trifluoromethyl), $R^2$ is hydrogen, C1–8 alkyl, halogen, C1–4 alkoxy, C1–4 alkythio, nitro, NR$^7$R$^8$ (in which R$^7$ and R$^8$ each independently, is C1–4 alkyl), cyano, trifluoromethyl or trifluoromethyloxy, $R^3$ and $R^4$ each independently, is hydrogen or C1–4 alkyl or $R^3$ and $R^4$ taken together with carbon atom to which is attached represents C3–7 cycloalkylene, $R^5$ is —COOR$^9$ (in which R$^9$ is hydrogen or C1–4 alkyl) or heterocyclic ring which is equivalent to carboxylic acid,

is oxazole,

is phenyl or pyridinyl, and n is 1–3) a non-toxic salt thereof, or a hydrate thereof.

2. A compound according to claim 1, wherein Cyc1 is

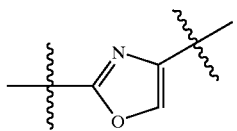

a non-toxic salt thereof, or a hydrate thereof.

3. A compound according to claim 1, wherein $A^2$ is C3–8 alkynylene or non-toxic salt thereof, or hydrate thereof.

4. A compound according to claim 1, wherein $R^1$ is —COOR$^9$ (in which $R^9$ is hydrogen or C1–4 alkyl) or non-toxic salt thereof, or hydrate thereof.

5. A compound according to claim 1, wherein $R^5$ is —COOR$^9$ (in which $R^9$ is hydrogen or C1–4 alkyl), $A^2$ is C3–8 alkynylene, Cyc1 is

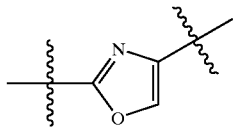

or non-toxic salt thereof, or hydrate thereof.

6. A compound according to claim 1, which is
(1) 2-((2E)-4-(2-(5-methyl-2-phenyloxazol-4-yl)ethoxy)-2-butenylthio)acetic acid methyl ester,
(2) 2-((2Z)-4-(2-(5-methyl-2-phenyloxazol-4-yl)ethoxy)-2-butenylthio)acetic acid methyl ester,
(3) 2-(4-(2-(5-methyl-2-phenyloxazol-4-yl)ethoxy)-2-butynylthio)acetic acid methyl ester,
(4) 2-((2E)-2-methyl-4-(2-(5-methyl-2-phenyloxazol-4-yl)ethoxy)-2-butenylthio)acetic acid methyl ester,
(5) 2-((2E)-3-methyl-4-(2-(5-methyl-2-phenyloxazol4-yl)ethoxy)-2-butenylthio)acetic acid methyl ester,
(6) 2-((2E)-4-(2-(5-methyl-2-(4-methylphenyl)oxazol-4-yl)ethoxy)-2-butenylthio)acetic acid methyl ester,
(8) 2-(4-(2-(5-methyl-2-(4-methylphenyl)oxazol-4-yl)ethoxy)-2-butynylthio)acetic acid methyl ester,
(10) 2-(4-(2-(5-methyl-2-(4-ethylphenyl)oxazol-4-yl)ethoxy)-2-butynylthio)acetic acid methyl ester,
(11) 2-(4-(2-(5-methyl-2-(4-propylphenyl)oxazol-4-yl)ethoxy)-2-butynylthio)acetic acid methyl ester,
(12) (2RS)-2-(4-(2-(5-methyl-2-(4-methylphenyl)oxazol-4-yl)ethoxy)-2-butynylthio)propanoic acid methyl ester,
(13) 2-methyl-2-(4-(2-(5-methyl-2-(4-methylphenyl) oxazol-4 -yl )ethoxy)-2-butynylthio)propanoic acid ethyl ester,
(14) 1-(4-(2-(5-methyl-2-(4-methylphenyl)oxazol-4-yl)ethoxy)-2-butynylthio)cyclobutane carboxylic acid ethyl ester,
(15) 2-(4-(2-(5-methyl-2-(4-dimethylaminophenyl)oxazol-4-yl)ethoxy)-2-butynylthio)acetic acid ethyl ester,
(16) 2-(4-(2-(5-methyl-2-(2-dimethylaminopyridin-5-yl)oxazol-4-yl)ethoxy)-2-butynylthio)acetic acid methyl ester,
(17) 2-methyl-2-(4-(2-(5-methyl-2-(4-dimethylaminophenyl)oxazol-4-yl )ethoxy)-2-butynylthio)propanoic acid ethyl ester,
(18) 1-(4-(2-(5-methyl-2-(4-dimethylaminophenyl) oxazol-4-y 1)ethoxy-2-butynylthio)cyclobutane carboxylic acid ethyl ester,
(19) 2-methyl-2-(4-(2-(5-methyl-2-(2-dimethylaminopyridin-5-yl)oxazol-4-yl)ethoxy)-2-butynylthio)propanoic acid ethyl ester,
(20) 1-(4-(2-(5.-methyl-2-(2-dimethylaminopyridin-5-yl)oxazol-4-yl)ethoxy-2-butynylthio)cyclobutane carboxylic acid ethyl ester,
(21) 2-(5-(2-(5-methyl-2-phenyloxazol-4-yl)ethoxy)pentylthio)acetic acid methyl ester,
(22) 2-(4-(2-(5-methyl-2-phenyloxazol-4-yl)ethoxy)butylthio)acetic acid methyl ester,
(23) 2-(3-(2-(5-methyl-2-phenyloxazol-4-yl)ethoxy)propylthio)acetic acid methyl ester,
(24) 2-((2E)4-(2-(5-methyl-2-phenyloxazol-4-yl)ethoxy)-2-butenylthio)acetic acid,
(25) 2-((2Z)-4-(2-(5-methyl-2-phenyloxazol-4-yl)ethoxy)-2-butenylthio)acetic acid,
(26) 2-(4-(2-(5-methyl-2-phenyloxazol-4-yl)ethoxy)-2-butynylthio)acetic acid,
(27) 2-((2E)-2-methyl-4-(2-(5-methyl-2-phenyloxazol4-yl)ethoxy)-2-butenylthio)acetic acid,
(28) 2-((2E)-3-methyl-4-(2-(5-methyl-2-phenyloxazol-4-yl)ethoxy)-2-butenylthio)acetic acid,
(29) 2-((2E)-4-(2-(5-methyl-2-(4-methylphenyl)oxazol-4-yl)ethoxy)-2-butenylthio)acetic acid,
(31) 2-(5-(2-(5-methyl-2-phenyloxazol-4-yl)ethoxy)pentylthio)acetic acid,
(32) 2-(4-(2-(5-methyl-2-phenyloxazol-4-yl)ethoxy)butylthio)acetic acid,
(33) 2-(3-(2-(5-methyl-2-phenyloxazol-4-yl)ethoxy)propylthio)acetic acid,
(34) 2-(4-(2-(5-methyl-2-(4-methylphenyl)oxazol-4-yl)ethoxy)-2-butynylthio)acetic acid,
(36) 2-(4-(2-(5-methyl-2-(4-ethylphenyl)oxazol-4-yl)ethoxy)-2-butynylthio)acetic acid,
(37) 2-(4-(2-(5-methyl-2-(4-propylphenyl)oxazol-4-yl)ethoxy)-2-butynylthio)acetic acid,
(38) 2-methyl-2-(4-(2-(5-methyl-2-(4-methylphenyl)oxazol-4-yl )ethoxy)-2-butynylthio)propanoic acid,
(39) 1-(4-(2-(5-methyl-2-(4-methylphenyl)oxazol-4-yl)ethoxy)-2-butynylthio)cyclobutane carboxylic acid,
(40) 2-(4-(2-(5-methyl-2-(4-dimethylaminophenyl)oxazol-4-yl)ethoxy)-2-butynylthio)acetic acid,
(41) 2-(4-(2-(5-methyl-2-(2-dimethylaminopyridin-5-yl)oxazol-4-yl)ethoxy)-2-butynylthio)acetic acid,
(42) 2-((2E)-4-(2-(5-methyl-2-phenyloxazol-4-yl)ethoxy)-2-butenylthio)acetic acid sodium salt,
(43) 2-((2Z)4-(2-(5-methyl-2-phenyloxazol-4-yl)ethoxy)-2-butenylthio)acetic acid sodium salt,
(44) 2-(4-(2-(5-methyl-2-phenyloxazol-4-yl)ethoxy)-2-butynylthio)acetic acid sodium salt,
(45) 2-((2E)-3-methyl-4-(2-(5-methyl-2-phenyloxazol-4-yl)ethoxy)-2-butenylthio)acetic acid sodium salt,
(46) 2-((2E)-4-(2-(5-methyl-2-(4-methylphenyl)oxazol-4-yl)ethoxy)-2-butenylthio)acetic acid sodium salt,
(48) 2-(5-(2-(5-methyl-2-phenyloxazol-4-yl)ethoxy)pentylthio)acetic acid sodium salt,
(49) 2-(4-(2-(5-methyl-2-phenyloxazol-4-yl)ethoxy)butylthio)acetic acid sodium salt,
(50) 2-(3-(2-(5-methyl-2-phenyloxazol-4-yl)ethoxy)propylthio)acetic acid sodium salt,
(51) (2RS)-2-(4-(2-(5-methyl-2-(4-methylphenyl)oxazol-4-yl)ethoxy)-2-butynylthio)propanoic acid sodium salt,

(52) 2-(4-(2-(5-methyl-2-(4-methylphenyl)oxazol-4-yl)ethoxy)-2-butynylsulfonyl)acetic acid,

(53) 2-(4-(2-(5-methyl-2-(4-methylphenyl)oxazol-4-yl)ethoxy)-2-butynylsulfonyl)acetic acid, or

(55) 7-(2-(5-methyl-2-(4-methylphenyl)oxazol-4-yl)ethoxy)-5-heptynoic acid, a non-toxic salt thereof, or a hydrate thereof.

7. A method for prevention and/or treatment of diseases induced by a peroxisome proliferator activated receptor which comprises administering to a subject in need thereof an effective amount of the compound of the formula (I), as claimed in claim 1, a non-toxic salt thereof, or a hydrate thereof.

8. The method of claim 7, wherein the peroxisome proliferator activated receptor is peroxisome proliferator activated receptor α and/or γ.

9. The method of claim 7, wherein said disease is hyperglycemia and hyperlipidermia.

10. The method of claim 7, wherein said disease is a metabolic disorder selected from the group consisting of diabetes, obesity, syndrome X, hypercholesterolemia, hyperlipoproteinemia, hyperlipidermia, atherosclerosis, hypertension, circulatory diseases, overeating and coronary heart diseases.

11. A method for elevating HDL cholesterol, which comprises administering to a subject in need thereof an effective amount of a compound of the formula (I), as claimed in claim 1, a non-toxic salt thereof, or a hydrate thereof.

12. A method for lowering LDL cholesterol or VDL cholesterol, which comprises administering to a subject in need thereof an effective amount of a compound of the formula (I), as claimed in claim 1, a non-toxic salt thereof, or a hydrate thereof.

13. A method for relief from risk factor of diabetes or syndrome X, which comprises administering to a subject in need thereof an effective amount of a compound of the formula (I), as claimed in claim 1, a non-toxic salt thereof, or a hydrate thereof.

* * * * *

SEQUENCE LISTING

<160> NUMBER OF SEQ ID NOS: 3

<210> SEQ ID NO 1
<211> LENGTH: 85
<212> TYPE: DNA
<213> ORGANISM: Artificial sequence
<220> FEATURE:
<223> OTHER INFORMATION: Enhancer sequence including 4 times repeated
      Gal4 protein response sequences

<400> SEQUENCE: 1
tcgacggagt actgtcctcc gcgacggagt actgtcctcc gcgacggagt actgtcctcc        60
gcgacggagt actgtcctcc gagct                                              85

<210> SEQ ID NO 2
<211> LENGTH: 9
<212> TYPE: PRT
<213> ORGANISM: Unknown
<220> FEATURE:
<223> OTHER INFORMATION: Nuclear localozation signal derived from SV-40
      T-antigen

<400> SEQUENCE: 2

Ala Pro Lys Lys Lys Arg Lys Val Gly
 1               5

<210> SEQ ID NO 3
<211> LENGTH: 9
<212> TYPE: PRT
<213> ORGANISM: Influenza virus
<220> FEATURE:
<223> OTHER INFORMATION: hemagglutinin epitope

<400> SEQUENCE: 3

Tyr Pro Tyr Asp Val Pro Asp Tyr Ala
 1               5